United States Patent [19]

Janssens et al.

[11] Patent Number: 5,278,165
[45] Date of Patent: Jan. 11, 1994

[54] OXAZOLYL IMIDAZOL[4,5-B]PYRIDIN AND PYRIMIDINE COMPOUNDS

[75] Inventors: Frans E. Janssens, Bonheiden; Francois M. Sommen, Wortel; Ann C. J. Dierckx, Kasterlee; Ludwig P. Cooymans, Beerse, all of Belgium

[73] Assignee: Janssen Pharmaceutica N.V., Beerse, Belgium

[21] Appl. No.: 35,854

[22] Filed: Mar. 23, 1993

Related U.S. Application Data

[60] Division of Ser. No. 723,862, Jul. 1, 1991, Pat. No. 5,217,980, which is a continuation-in-part of Ser. No. 554,326, Jul. 19, 1990, abandoned.

[51] Int. Cl.$^5$ .................. A61K 31/505; A61K 31/52; A61K 31/44; C07D 487/04
[52] U.S. Cl. .................... 514/258; 514/212; 514/255; 514/261; 514/262; 514/263; 514/265; 514/266; 514/303; 540/599; 540/600; 544/262; 544/264; 544/265; 544/268; 544/269; 544/270; 544/271; 544/272; 544/277; 544/278; 544/279; 544/281
[58] Field of Search .............. 514/212, 255, 258, 261, 514/262, 263, 265, 266, 303; 540/599, 600; 544/262, 264, 265, 268, 269, 270, 271, 272, 277, 278, 279, 281, 282, 284; 546/118

[56] References Cited

U.S. PATENT DOCUMENTS

| | | | |
|---|---|---|---|
| 4,556,660 | 12/1985 | Janssens et al. | 514/272 |
| 4,588,772 | 5/1986 | Bohmer et al. | 525/54.23 |
| 4,634,704 | 1/1987 | Janssens et al. | 514/253 |
| 4,695,569 | 9/1987 | Janssens et al. | 514/258 |
| 4,695,575 | 9/1987 | Janssens et al. | 514/322 |
| 4,835,161 | 5/1989 | Janssens et al. | 514/303 |
| 4,897,401 | 1/1990 | Janssens et al. | 514/303 |
| 4,988,689 | 1/1991 | Janssens et al. | 514/212 |
| 5,041,448 | 8/1991 | Janssens et al. | 514/266 |

Primary Examiner—Mukund J. Shah
Assistant Examiner—Y. N. Gupta
Attorney, Agent, or Firm—Charles J. Metz

[57] ABSTRACT

Oxazolyl derivatives of formula (I)

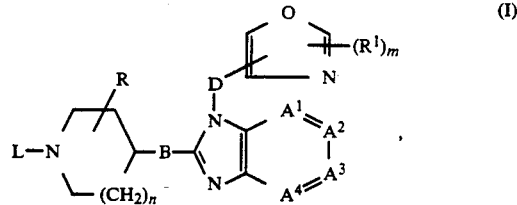

wherein $-A^1=A^2-A^3=A^4-$ represents a bivalent radical having the formula

| | |
|---|---|
| $-CH=CH-CH=CH-$ | (a-1), |
| $-N=CH-CH=CH-$ | (a-2), |
| $-CH=N-CH=CH-$ | (a-3), |
| $-CH=CH-N=CH-$ | (a-4), |
| $-CH=CH-CH=N-$ | (a-5), |
| $-N=CH-N=CH-$ | (a-6) | or

| | |
|---|---|
| $-CH=N-CH=N-$ | (a-7); |

R represents hydrogen or $C_{1-4}$alkyl; $R^1$ represents hydrogen, $C_{1-6}$alkyl or hydroxy$C_{1-6}$alkyl; m represents 1 or 2; D represents $C_{1-4}$alkanediyl; B represents $NR^2$, $CH_2$, O, S, SO or $SO_2$ wherein $R^2$ is hydrogen or $C_{1-4}$alkyl; n represents 0, 1 or 2; L represents hydrogen; $C_{1-12}$alkyl; $C_{3-6}$cycloalkyl; $C_{3-6}$alkenyl optionally substituted with aryl; $C_{1-6}$alkylcarbonyl; $C_{1-6}$alkyloxycarbonyl; arylcarbonyl; aryl$C_{1-6}$alkyloxycarbonyl; or a radical of formula $-Alk-R^3$ (b-1); $-Alk-Y-R^4$ (b-2); $-Alk-Z^1-C(=X)-Z^2-R^5$ (b-3); or $-CH_2-CHOH-CH_2-O-R^6$ (b-4), the pharmaceutically acceptable acid addition salts and stereochemically isomeric forms thereof have antiallergic properties. Compositions containing the same and methods of treating warm-blooded animals suffering from allergic diseases.

15 Claims, No Drawings

OXAZOLYL IMIDAZOL[4,5-B]PYRIDIN AND PYRIMIDINE COMPOUNDS

CROSS-REFERENCE TO RELATED APPLICATION

This application is a division of copending application Ser. No. 723,862, filed Jul. 1, 1991, now U.S. Pat. No. 5,217,980, which in turn was a continuation-in-part of application Ser. No. 554,326, filed Jul. 19, 1990, now abandoned.

BACKGROUND OF THE INVENTION

In U.S. Pat. No. 4,556,660, 4,634,704; 4,695,569; 4,695,575; 4,588,722; 4,835,161; 4,897,401 and in EP-A-0,206,415 and 0,297,661 there are disclosed benzimidazole and imidazopyridine substituted piperidine derivatives as antihistaminics and serotonin antagonists.

DESCRIPTION OF THE INVENTION

The present invention is concerned with novel oxazolyl derivatives having the formula:

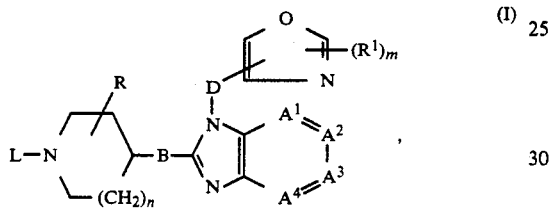

the pharmaceutically acceptable addition salts and the stereochemically isomeric forms thereof, wherein
—$A^1$=$A^2$—$A^3$=$A^4$— represents a bivalent radical having the formula —CH=CH—CH=CH—     (a-1), —N=CH—CH=CH—     (a-2), —CH=N—CH=CH—     (a-3), —CH=CH—N=CH—     (a-4), —CH=CH—CH=N—     (a-5), —N=CH—N=CH—     (a-6)

or

—CH=N—CH=N—(a-7);

wherein one or two hydrogen atoms in said radicals (a-1) to (a-7) may each independently be replaced by halo, $C_{1-6}$alkyl, $C_{1-6}$alkyloxy, hydroxy or trifluoromethyl;
R represents hydrogen or $C_{1-4}$alkyl;
$R^1$ represents hydrogen, $C_{1-6}$alkyl or hydroxy$C_{1-6}$alkyl;
m is 1 or 2;
D represents $C_{1-4}$alkanediyl;
B represents $NR^2$, $CH_2$, O, S, SO or $SO_2$ wherein $R^2$ is hydrogen or $C_{1-4}$alkyl;
n is 0, 1 or 2;
L represents hydrogen; $C_{1-12}$alkyl; $C_{3-6}$cycloalkyl; $C_{3-6}$alkenyl optionally substituted with aryl; $C_{1-6}$alkylcarbonyl; $C_{1-6}$alkyloxycarbonyl; arylcarbonyl; aryl$C_{1-6}$alkyloxy-carbonyl; or a radical of formula:

—Alk—$R^3$     (b-1);

—Alk—Y—$R^4$     (b-2);

—Alk—$Z^1$—C(=X)—$X^2$—$R^5$     (b-3);

or

—$CH_2$—CHOH—$CH_2$O—$R^6$     (b-4);

wherein
$R^3$ represents cyano, aryl or Het;
$R^4$ represents hydrogen, aryl, Het or $C_{1-6}$alkyl optionally substituted with aryl or Het;
$R^5$ represents hydrogen, aryl, Het or $C_{1-6}$alkyl optionally substituted with aryl or Het;
$R^6$ represents aryl or naphthalenyl;
Y represents O, S, $NR^7$; said $R^7$ being hydrogen, $C_{1-6}$alkyl or $C_{1-6}$alkylcarbonyl;
$Z^1$ and $Z^2$ each independently represent O, S, $NR^8$ or a direct bond; said $R^8$ being hydrogen or $C_{1-6}$alkyl;
X represents O, S or $NR^9$; said $R^9$ being hydrogen, $C_{1-6}$alkyl or cyano;
each Alk independently is $C_{1-6}$alkanediyl;
each Het represents:
(i) an optionally substituted five- or six-membered heterocyclic ring containing 1, 2, 3 or 4 heteroatoms selected from oxygen, sulfur and nitrogen, provided that no more than 2 oxygen and/or sulfur atoms are present;
(ii) an optionally substituted five- or six-membered heterocyclic ring containing 1 or 2 heteroatoms selected from oxygen, sulfur and nitrogen, being fused with an optionally substituted five- or six-membered ring through 2 carbon atoms or 1 carbon and 1 nitrogen atom, containing in the remainder of the fused ring only carbon atoms; or
(iii) an optionally substituted five- or six-membered heterocyclic ring containing 1 or 2 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;
wherein Het being a monocyclic ring system may be optionally substituted with up to 4 substituents; and wherein Het being a bicyclic ring system may be optionally substituted with up to 6 substituents, said substituents being selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, $C_{1-6}$alkyloxy$C_{1-6}$alkyl, $C_{1-6}$alkyloxycarbonyl$C_{1-6}$alkyl, hydroxy, mercapto, hydroxy$C_{1-6}$alkyl, $C_{1-6}$alkylcarbonyloxy, aryl, aryl$C_{1-6}$alkyl, carboxyl, $C_{1-6}$alkylaminocarbonylamino, arylaminocarbonylamino, oxo or thio;
each aryl is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl and $C_{1-6}$alkylcarbonyl.

In the compounds of formula (I) where $R^3$, $R^4$ or $R^5$ is Het, said Het may be partly or completely saturated, or unsaturated. The compounds of formula (I) wherein Het is partly saturated or unsaturated and is substituted with hydroxy, mercapto or amino, may also exist in their tautomeric forms. Such forms although not explicitly indicated hereinabove, are intended to be included within the scope of the invention.

As used in the foregoing definitions halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1,1-dimethylethyl, 1-methylpropyl, 2-methylpropyl; $C_{1-6}$alkyl defines $C_{1-4}$alkyl radicals as defined hereinabove and the higher homologs thereof having 5 or 6 carbon atoms; $C_{1-12}$alkyl defines $C_{1-4}$alkyl radicals as defined hereinabove and the higher homologs thereof having from 5 to 12 carbon atoms; $C_{3-6}$cycloalkyl is generic to cyclopropyl, cyclobutyl, cyclopentyl and cyclohexyl; $C_{3-6}$alkenyl defines straight and branch chain hydrocarbon radicals containing one double bond and having from 3 to 6 carbon atoms such as, for example, 2-propenyl, 3-butenyl, 2-butenyl, 2-pentenyl, 3-pentenyl, 3-methyl-2-butenyl and the like; and when a $C_{3-6}$-alkenyl is substituted on a heteroatom, then the carbon atom of said $C_{3-6}$alkenyl connected to said heteroatom, preferably is saturated; $C_{1-4}$alkanediyl defines bivalent straight and branch chained saturated hydrocarbon radicals having from 1 to 4 carbon atoms such as, for example, methylene, 1,2-ethanediyl, 1,3-propanediyl, 1,4-butanediyl and the branched isomers thereof; $C_{1-6}$alkanediyl defines $C_{1-4}$alkanediyl radicals as defined hereinabove and the higher homologs thereof having 5 or 6 carbon atoms such as, for example, 1,5-pentanediyl, 1,6-hexanediyl and the branched isomers thereof.

The pharmaceutically acceptable addition salts as mentioned hereinabove comprise the therapeutically active non-toxic acid addition salt forms which the compounds of formula (I) are able to form. Said salt forms can conveniently be obtained by treating the base form of the compounds of formula (I) with appropriate acids such as inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The compounds of formula (I) having acidic properties may be converted in a similar manner into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, N-methyl-D-glucamine, hydrabamine, amino acids, e.g. arginine, lysine.

The term acid addition salt also comprises the hydrates and solvent addition forms which the compounds of formula (I) are able to form. Examples of such forms are e.g. hydrates, alcoholates and the like.

The compounds of this invention may have several asymmetric carbon atoms in their structure. Each of these chiral centers may be indicated by the stereochemical descriptors R and S.

Pure stereochemically isomeric forms of the compounds of formula (I) may be obtained by the application of art-known procedures. Diastereoisomers may be separated by physical methods such as selective crystallization and chromatographic techniques. e.g. counter current distribution, liquid chromatography and the like; and enantiomers may be separated from each other following art-known resolution methods, for example, by the selective crystallization of their diastereometic salts with chiral acids. Pure stereochemically isomeric forms may also be derived from the corresponding pure stereochemically isomeric forms of the appropriate starting materials, provided that the reactions occur stereospecifically. Preferably, if a specific stereoisomer is desired, said compound will be synthesized by stereoselective methods of preparation. These methods will advantageously employ enantiomerically pure starting materials. Stereochemically isomeric forms of the compounds of formula (I) are obviously intended to be included within the scope of the invention.

In particular, the radical Het as defined hereinabove may be selected from pyridinyl, optionally substituted with one or two substituents each independently selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxycarbonyl, hydroxy, $C_{1-6}$alkylcarbonyloxy, aryl$C_{1-6}$alkyl and carboxyl; pyridinyloxide, optionally substituted with nitro; pyrimidinyl, optionally substituted with one or two substituents each independently selected from halo, amino, $C_{1-6}$alkylamino, aryl$C_{1-6}$alkylamino, hydroxy, $C_{1-6}$alkyl, $C_{1-6}$alkyloxy, $C_{1-6}$alkylthio and aryl$C_{1-6}$alkyl; pyridazinyl, optionally substituted with $C_{1-6}$alkyl or halo; pyrazinyl, optionally substituted with halo, amino or $C_{1-6}$alkyl; thienyl, optionally substituted with halo or $C_{1-6}$alkyl; furanyl, optionally substituted with halo or $C_{1-6}$alkyl pyrrolyl, optionally substituted with $C_{1-6}$alkyl; thiazolyl, optionally substituted with $C_{1-6}$alkyl, $C_{1-6}$alkyloxycarbonyl, aryl or aryl$C_{1-6}$alkyl; imidazolyl, optionally substituted with one or two substituents each independently selected from $C_{1-6}$alkyl, aryl$C_{1-6}$alkyl and nitro; tetrazolyl, optionally substituted with $C_{1-6}$alkyl; 1,3,4-thiadiazolyl, optionally substituted with $C_{1-6}$alkyl or amino; 5,6-dihydro-4H-1,3-thiazin-2-yl, optionally substituted with $C_{1-6}$alkyl; 4,5-dihydrothiazolyl, optionally substituted with $C_{1-6}$alkyl; oxazolyl, optionally substituted with $C_{1-6}$alkyl; 4,5-dihydro-5-oxo-1H-tetrazolyl, optionally substituted with $C_{1-6}$alkyl; 1,4-dihydro-2,4-dioxo-3(2H)-pyrimidinyl, optionally substituted with $C_{1-6}$alkyl; 1,4-dihydro-4-oxopyrimidinyl, 3,4-dihydro-4-oxopyrimidinyl or 4,5-dihydro-4-oxopyrimidinyl, said radicals optionally substituted with up to 3 substituents selected from $C_{1-6}$alkyl, amino, $C_{1-6}$alkylaminocarbonylamino, arylaminocarbonylamino, aryl$C_{1-6}$alkylamino and $C_{1-6}$alkylamino; 2,3-dihydro-3-oxopyridazinyl, optionally substituted with $C_{1-4}$alkyl; 2-(amino- or $C_{1-4}$alkylamino)-3,4-dihydro-3,6-dimethyl-4-oxopyrimidin-5-yl; 2-oxo-3-oxazolidinyl; pyrrolidinyl; piperidinyl; morpholinyl; thiomorpholinyl; dioxanyl, optionally substituted with $C_{1-6}$alkyl; indolyl, optionally substituted with hydroxy or $C_{1-6}$alkyl; quinolinyl, optionally substituted with hydroxy or $C_{1-6}$alkyl; quinazolinyl, optionally substituted with hydroxy or $C_{1-6}$alkyl; quinoxalinyl, optionally substituted with $C_{1-6}$alkyl, phthalazinyl, optionally substituted with halo; 1,3-dioxo-1H-isoindol-2(3H)-yl; 2,3-dihydro-3-oxo-4H-benzoxazinyl and 2,3-dihydro-1,4-benzodioxinyl, both being optionally substituted with $C_{1-6}$alkyl or halo; 2-oxo-2H-1-benzopyranyl and 4-oxo-4H-1-benzopyranyl, both being optionally substituted with $C_{1-6}$alkyl; 3,4-dihydro-1,3-dimethyl-2,6-dioxo-1H-purin-7-yl, optionally substituted with $C_{1-6}$alkyl; 6-purinyl, and a bicyclic heterocyclic radical of formula

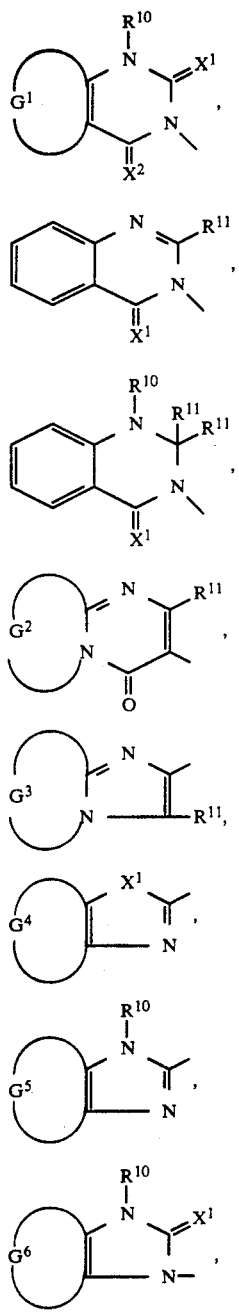

(c-1)

(c-2)

(c-3)

(c-4)

(c-5)

(c-6)

(c-7)

(c-8)

wherein
$X^1$ and $X^2$ each independently are O or S;

each $R^{10}$ independently is hydrogen, $C_{1-6}$alkyl, aryl$C_{1-6}$alkyl, $C_{1-6}$alkyloxy$C_{1-6}$alkyl, hydroxy$C_{1-6}$alkyl or $C_{1-6}$alkyloxycarbonyl;

each $R^{11}$ independently is hydrogen, $C_{1-6}$alkyl, hydroxy, mercapto, $C_{1-6}$alkyloxy, $C_{1-6}$alkylthio, halo or $C_{1-6}$alkyloxycarbonyl$C_{1-6}$alkyl;

$G^1$ is —CH=CH—CH=CH—; —S—CH=CH— or —N=CH—NH—;

$G^2$ is —CH=CH—CH=CH—, —(CH$_2$)$_4$—, —S—(CH$_2$)$_2$—, —S—(CH$_2$)$_3$—, S—CH=CH—, —CH=CH—O—, —NH—(CH$_2$)$_2$—, —NH—(CH$_2$)$_3$—, —NH—CH=CH—, —NH—N=CH—CH$_2$—, —NH—CH=N— or —NH—N=CH—;

$G^3$ is —CH=CH—CH=CH—, —CH$_2$—NH—(CH$_2$)$_2$—, —S—CH=CH—, —S—(CH$_2$)$_3$—, —N=CH—CH=CH—, —CH=N—CH=CH—, —CH=CH—N=CH—, —CH=CH—CH=N—, —N=CH—N=CH— or —CH=N—CH=N—;

$G^4$ is —CH=CH—CH=CH—, —CH$_2$—NH—(CH$_2$)$_2$—, —N=CH—CH=CH—; —CH=N—CH=CH—, —CH=CH—N=CH—, —CH=CH—CH=N—, —N=CH—N=CH= or —CH=N—CH=N—;

$G^5$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

$G^6$ is —CH=CH—CH=CH—, —N=CH—CH=CH—, —CH=N—CH=CH—, —CH=CH—N=CH—, —CH=CH—CH=N—, —N=CH—N=CH— or —CH=N—CH=N—;

wherein one or two hydrogen atoms in the benzene part of the radicals of formula (c-2) or (c-3) or one or two hydrogen atoms in said radicals $G^1$, $G^2$, $G^3$, $G^4$, $G^5$ or $G^6$ may be replaced by $C_{1-6}$alkyl, $C_{1-6}$alkylthio, $C_{1-6}$alkyloxy or halo, when connected to a carbon atom; or by $C_{1-6}$alkyl, $C_{1-6}$alkyloxycarbonyl or aryl$C_{1-6}$alkyl when connected to a nitrogen atom; and aryl is as defined hereinabove.

Aryl as used in the definition of $R^3$, $R^4$ and $R^5$, in particular is phenyl optionally substituted with halo, $C_{1-6}$alkyl, hydroxy or $C_{1-6}$alkyloxy; aryl as used in the definition of $R^6$ in particular is phenyl optionally substituted with halo.

Particular compounds are those compounds of formula (I) wherein R represents hydrogen; m is 1; and $R^1$ represents hydrogen or $C_{1-6}$alkyl.

A particular subgroup among the compounds of formula (I) comprises those compounds of formula (I) wherein —A$^1$=A$^2$—A$^3$=A$^4$— is a bivalent radical of formula (a-1) or (a-2); another particular subgroup among the compounds of formula (I) comprises those compounds of formula (I) wherein —A$^1$=A$^2$—A$^3$=A$^4$— is a bivalent radical having a formula (a-3) through (a-5); wherein one or two hydrogen atoms in said radicals (a-1) to (a-5) may each independently be replaced by $C_{1-6}$alkyloxy or hydroxy.

More particular compounds are those compounds of any of the former groups or subgroups wherein B is NR$^2$, O or CH$_2$; and/or L is hydrogen, $C_{1-6}$alkyl, $C_{1-6}$alkylcarbonyl, $C_{1-6}$alkyloxycarbonyl, or a radical of formula (b-1), (b-2), (b-3) or (b-4).

Still more particular compounds are those more particular compounds of formula (I)
B is NH or CH$_2$; and/or n is 1 or 2; and/or the moiety

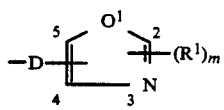

is (2- wherein or
4-C$_{1-4}$alkyl-1,3-oxazol-5-yl)-C$_{1-4}$alkyl; (2- or 5-C$_{1-4}$alkyl-1,3-oxazol-4-yl)C$_{1-4}$alkyl; (4- or 5-C$_{1-4}$alkyl-1,3-oxazol-2-yl)C$_{1-4}$alkyl, 1,3-oxazol-2-yl; 1,3-oxazol-4-yl; 1,3-oxazol-5-yl; (2- or 4-hydroxymethyl-1,3-oxazol-5-yl)C$_{1-4}$alkyl; (2- or 5-hydroxymethyl-1,3-oxazol-4-yl)C$_{1-4}$alkyl; (4- or 5-hydroxymethyl-1,3-oxazol-2-yl)C$_{1-4}$alkyl; (2,4-di(C$_{1-4}$alkyl)-1,3-oxazol-5-yl)C$_{1-4}$alkyl; (2,5-di(C$_{1-4}$alkyl)-1,3-oxazol-4-yl)C$_{1-4}$alkyl or (4,5-di(C$_{1-4}$alkyl)-1,3-oxazol-2-yl)C$_{1-4}$alkyl.

Interesting compounds within the present invention are those compounds of formula (I) wherein —A$^1$=A$^2$—A$^3$=A$^4$— represents a bivalent radical having the formula —CH=CH—CH=CH— (a-1) or —N=CH—CH=CH— (a-2), wherein one hydrogen atom in said radical (a-1) may be replaced by halo, C$_{1-6}$alkyloxy or hydroxy; R represents hydrogen or methyl; R$^1$ represents hydrogen, methyl or hydroxymethyl; m is 1 or 2; D represents CH$_2$; B represents NH, NCH$_3$, CH$_2$, O, S or SO; n is 0, 1 or 2; L represents hydrogen; C$_{1-4}$alkyl; cyclohexyl; propenyl, 3-phenylpropenyl; C$_{1-4}$alkyloxycarbonyl; or a radical of formula:

—Alk—R$^3$ (b-1);

—Alk—Y—R$^4$ (b-2);

—Alk—Z$^1$—C(=X)—Z$^2$—R$^5$ (b-3);

or

—CH$_2$—CHOH—CH$_2$—O—R$^6$ (b-4);

wherein
each Alk independently represents C$_{1-4}$alkanediyl; R$^3$ represents phenyl, hydroxyphenyl, C$_{1-4}$alkyloxyphenyl, 3,4,5-trimethoxyphenyl, pyridinyl, thienyl, 2-methyl-5-oxazolyl, 4,5-dihydro-4-ethyl-5-oxo-1H-tetrazolyl, 2,3-dihydro-6-methyl-3-oxopyridazinyl, 2-oxo-3-oxazolidinyl, 2-(amino or methylamino)-3,4-dihydro-3,6-dimethyl-4-oxo-5-pyrimidinyl, 2-oxo-2H-1-benzopyranyl, 3,7-dihydro-1,3-dimethyl-2,6-dioxo-1H-purin-7-yl, 2,3-dihydro-2-oxo-1-benzimidazolyl or a radical of formula

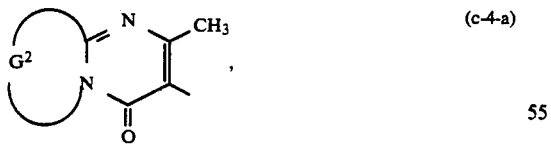

wherein G$^2$ represents —CH=CH—CH=CH—, —(CH$_2$)$_4$—, —S—(CH$_2$)$_2$—, —S—(CH$_2$)$_3$—, —S—CH=CH—, —N(CH$_2$)$_3$, —N=C(CH$_3$)—CH$_2$, —N(CH$_3$)—N=C(CH$_3$)—; —N(CH$_3$)—CH=CH— or CH=C(CH$_3$)—O—; Y represents NH, O or S; R$^4$ represents hydrogen, C$_{1-4}$alkyl, halophenyl, pyridinyl, halopyridinyl, pyrimidinyl, 1,4-dihydro-2,4-dioxo-3(2H)-pyrimidinyl, 1,4-dihydro-4-oxopyrimidinyl, pyridazinyl, halopyridazinyl, 1-methylimidazloyl, 1-methylimidazolyl, thiazolyl, 2-amino-1,3,4-thiadiazolyl, 6-purinyl or imidazo[4,5-c]pyridinyl; Z$^1$ and Z$^2$ each independently represent O, NH or a direct bond; X represents O or S; R$^5$ represents hydrogen, C$_{1-4}$alkyl, aminophenyl, C$_{1-4}$alkylphenyl, pyridinyl, aminopyridinyl, aminopyrazinyl, 1-methylpyrrolyl, furanyl or 1-methylindolyl; and R$^6$ represents phenyl.

Particularly interesting compounds are those interesting compounds wherein —A$^1$=A$^2$—A$^3$=A$^4$— represents a bivalent radical having the formula —CH=CH—CH=CH— (a-1) or —N=CH—CH=CH— (a-2), R represents hydrogen; the oxazolyl moiety has the formula

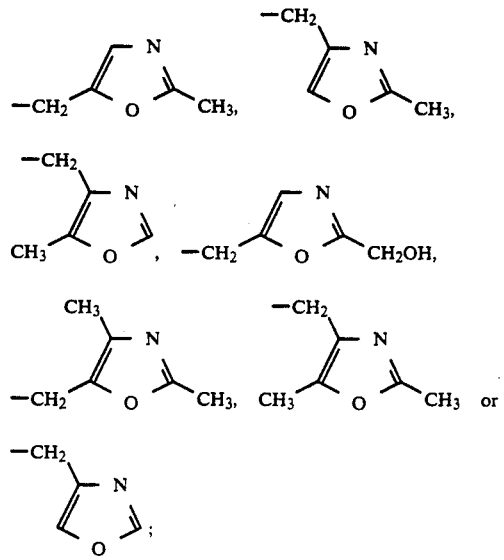

B represents NH, S or CH$_2$; n is 1; L represents hydrogen, C$_{1-4}$alkyl, hydroxyC$_{1-4}$alkyl, propenyl, 3-phenylpropenyl or a radical of formula —Alk—R$^3$ (b-1);

—Alk—Y—R$^4$ (b-2);

—Alk—NH—C(=O)—R$^{5-a}$ (b-3-a);

or

—Alk—C(=O)—Z$^2$—R$^{5-b}$ (b-3-b);

wherein each Alk independently represents C$_{1-3}$alkanediyl; R$^3$ represents phenyl, 4-methoxyphenyl, 4-hydroxyphenyl, pyridinyl, thienyl, 4,5-dihydro-4-ethyl-5-oxo-1H-tetrazolyl, 2-oxo-2H-1-benzopyranyl, 2-(amino- or methylamino)-3,4-dihydro-3,6-dimethyl-4-oxo-5-pyrimidinyl, 6-purinyl, or a radical of formula

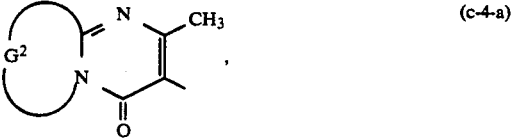

wherein G$^2$ represents —CH=CH—CH=CH—, —(CH$_2$)$_4$—, —S—(CH$_2$)$_2$—, —S—(CH$_2$)$_3$—, —S—CH=CH— or —N(CH$_3$)—N=C(CH$_3$)—CH$_2$—; Y represents NH or O; R$^4$ represents pyrimidinyl, 5-amino-1,3,4-thiadiazolyl, pyridazinyl, imidazo[4,5-c]pyridinyl or 1,4-dihydro-4-oxo-2-pyrimidinyl, R$^{5-a}$ represents aminopyrazinyl or furanyl; $Z^2$ represents O; and $R^{5\text{-}b}$ represents hydrogen.

Preferred compounds are any compounds of the above defined groups wherein —$A^1$=$A^2$—$A^3$=$A^4$— is a bivalent radical of formula —CH=CH—CH=CH— (a-1) or —N=CH—CH=CH— (a-2); wherein one or two hydrogen atoms in said radicals (a-1) or (a-2) may each independently be replaced by halo, $C_{1\text{-}6}$alkoxy or hydroxy; D is CH$_2$; and the oxazolyl radical connected to D has the formula

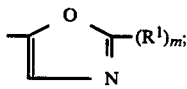

and/or L is hydrogen; $C_{1\text{-}6}$alkyl; a radical of formula (b-1) wherein $R^3$ is aryl or Het; a radical of formula (b-2) wherein Y is NH or O and $R^4$ is aryl or Het; or a radical of formula —Alk—NH—CO—Het (b-3-a); wherein each Het is pyridinyl, optionally substituted with amino or $C_{1\text{-}6}$alkyl; pyrimidinyl, optionally substituted with amino or $C_{1\text{-}6}$alkyl; pyrazinyl, optionally substituted with amino; thienyl; furanyl; thiazolyl, optionally substituted with $C_{1\text{-}6}$alkyl; imidazolyl, optionally substituted with $C_{1\text{-}6}$alkyl; tetrazolyl, optionally substituted with $C_{1\text{-}6}$alkyl; 1,3,4-thiadiazolyl, optionally substituted with $C_{1\text{-}6}$alkyl, or amino; oxazoloyl, optionally substituted with $C_{1\text{-}6}$alkyl; 4,5-dihydro-5-oxo-1H-tetrazolyl, optionally substituted with $C_{1\text{-}6}$alkyl; 1,4-dihydro-2,4-dioxo-3(2H)-pyrimidinyl; 3,4-dihydro-4-oxopyrimidinyl optionally substituted with up to 3 substituents selected from $C_{1\text{-}6}$alkyl, amino and $C_{1\text{-}6}$alkylamino; 2-oxo-3-oxazolidinyl; indolyl, optionally substituted with $C_{1\text{-}6}$alkyl; phthalazinyl; 2-oxo-2H-1-benzopyranyl; 3,7-dihydro-1,3-dimethyl-2,6-dihydro-1H-purin-7-yl, optionally substituted with $C_{1\text{-}6}$alkyl; 6-purinyl, or a bicyclic heterocyclic radical of formula (c-1) to (c-8) as defined hereinabove, wherein $R^{10}$ and $R^{11}$ each independently are hydrogen or $C_{1\text{-}6}$alkyl and in the radicals (c-2) and (c-3), $X^1$ is O, and;

each aryl is unsubstituted phenyl; phenyl substituted with 1 or 2 substituents each independently selected from halo, hydroxy, nitro, cyano, trifluoromethyl, $C_{1\text{-}6}$alkyl and $C_{1\text{-}6}$alkyloxy; and optionally further substituted with a third substituent selected from halo, $C_{1\text{-}6}$alkyl or $C_{1\text{-}6}$alkyloxy.

More preferred compounds are those preferred compounds wherein L is hydrogen or $C_{1\text{-}3}$alkyl.

Further more preferred compounds are those preferred compounds wherein L is a radical of formula —Alk—$R^3$ (b-1) wherein $R^3$ is 4-methoxyphenyl; 4-hydroxyphenyl; thienyl; thiazolyl optionally substituted with $C_{1\text{-}6}$alkyl; oxazolyl; 4,5-dihydro-1H-tetrazolyl optionally substituted with $C_{1\text{-}6}$alkyl; 2,3-dihydro-2-oxobenzimidazol-1-yl; 1,4-dihydro-2,4-dioxo-3(2H)-pyrimidinyl; thienyl; 2-oxo-2H-1-benzopyranyl or $R^3$ is a radical of formula

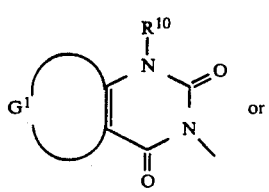

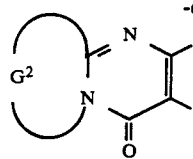

wherein $G^1$, $G^2$ and $R^{10}$ are as defined hereinabove.

Still other more preferred compounds are those preferred compounds wherein L is a radical of formula —Alk—Y—$R^4$ (b-2) wherein Y is NH or O and $R^4$ is thiazolyl, pyridinyl, 1,3,4-thiadiazolyl optionally substituted with $C_{1\text{-}6}$alkyl or amino, pyrimidinyl optionally substituted with amino, 6-purinyl, 3,4-dihydro-4-oxopyrimidinyl, phthalazinyl or 3H-imidazo[4,5-c]pyridin-2-yl.

The most preferred compound is 1-[2-methyl-5-oxazolyl)methyl]-N-(1-methyl-4-piperidinyl)-1H-benzimidazol-2-amine, the solvates and the pharmaceutically acceptable addition salts thereof.

In order to simplify the structural representation of some of the compounds and intermediates in the following preparations the moiety containing the imidazol group fused to a benzene, pyridine or pyrimidine ring will hereinafter be represented by the symbol Q.

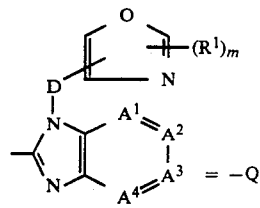

The compounds of formula (I) can generally be prepared by reacting an intermediate of formula (II) with an appropriately substituted diamine of formula (III).

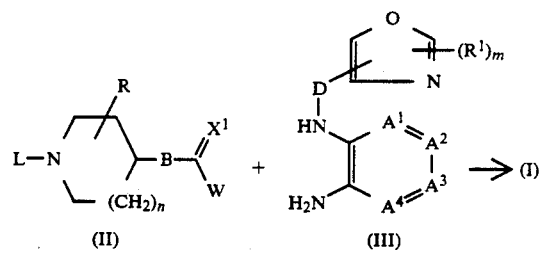

In this and the following reaction schemes W represents an appropriate reactive leaving group such as, for example, halo, e.g. chloro, bromo or iodo; $C_{1\text{-}6}$alkyloxy; $C_{1\text{-}6}$alkylthio, aryloxy or arylthio; and $X^1$ denotes O, S or NH.

The derivatives of formula (II) wherein B is CH$_2$ and W is halo may be generated in situ, for example, by halogenating the corresponding carboxylic acid with thionyl chloride, phosphorous trichloride, phosphoryl chloride, polyphosphoric acid and the like reagents. The reaction of (II) with (III) may be conducted in a suitable reaction-inert solvent such as, for example, a hydrocarbon, e.g., benzene, hexane and the like; an ether, e.g., 1,1'-oxybisethane, tetrahydrofuran and the like; a ketone, e.g., 2-propanone, 2-butanone and the like; an alcohol, e.g., methanol, ethanol, 2-propanol, 1-butanol and the like; a halogenated hydrocarbon, e.g., trichloromethane, dichloromethane and the like; an organic acid, e.g., acetic acid, propanoic acid and the like; a dipolar aprotic solvent e.g., N,N-dimethylformamide, N,N-dimethylacetamide and the like; or a mixture of such solvents. Depending upon the nature of the solvent and W it may be appropriate to add to the reaction mixture a base such as is commonly employed in the art of conducting N-alkylation reactions and/or a iodide salt such as an alkali metal iodide. Elevated temperatures and stirring may enhance the reaction rate.

In some instances the reaction of (II) with (III) may first yield an intermediate of formula (II-a) which subsequently may be cyclized to the desired compound of formula (I), either in situ, or, if desired, after isolation and purification.

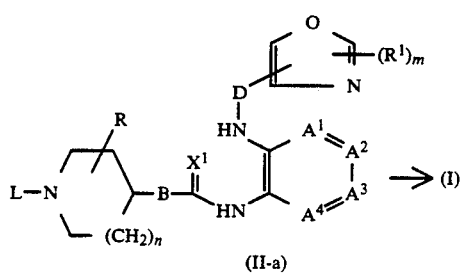

(II-a)

The compounds of formula (I) can also be prepared by reacting an intermediate of formula (IV) with an intermediate of formula (V) following art-known substitution reaction procedures. In (IV) and hereinafter, M is hydrogen when B is other than $CH_2$, or M represents an alkali or earth alkaline metal such as, for example, lithium or magnesium, when B represents $CH_2$.

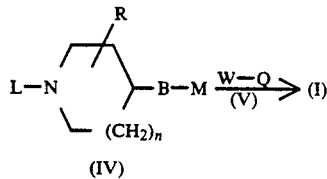

(IV)

Similarly, the compounds of formula (I) can also be prepared by reacting an intermediate of formula (VI) with an intermediate of formula (VII) wherein M has the previously defined meaning. In formula (VI) and hereinafter $W^1$ represents an appropriate leaving group such as, for example, halo, e.g., chloro, bromo and the like; or a sulfonyloxy group such as, for example, methanesulfonyloxy, 4-methylbenzenesulfonyloxy and the like.

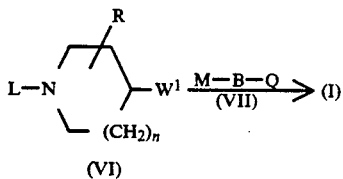

(VI)

The compounds of formula (I) wherein B is —$CH_2$—, said compounds being represented by formula (I-a), can also be prepared by reacting an intermediate of formula (VIII) with an intermediate of formula (IX) or alternatively, by reacting an intermediate of formula (X) with an intermediate of formula (XI).

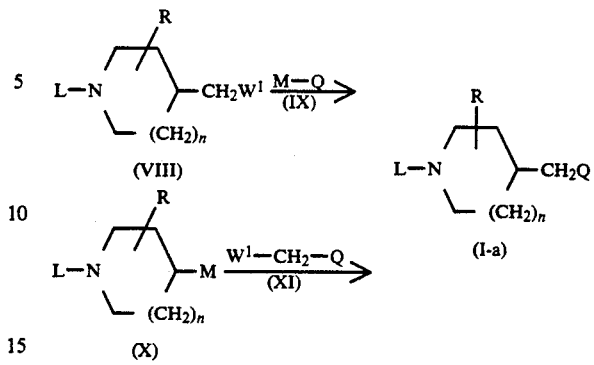

The reactions of (IV), (VI), (VIII) and (X) with respectively (V), (VII), (IX) and (XI) may conveniently be conducted in an appropriate reaction-inert solvent such as for example, an aromatic hydrocarbon, e.g., benzene, methylbenzene and the like; an ether, e.g. 1,4-dioxane, 1,1'-oxybisethane, tetrahydrofuran and the like; a halogenated hydrocarbon, e.g. trichloromethane and the like; N,N-dimethylformamide; N,N-dimethylacetamide; nitrobenzene; dimethylsulfoxide; 1-methyl-2-pyrrolidinone and the like; and when M is halogen, said solvent may also be a $C_{1-6}$alkanol, e.g., methanol, ethanol, 1-butanol and the like; a ketone, e.g., 2-propanone, 4-methyl-2-pentanone and the like. In some instances, particularly when B is a heteroatom, the addition of an appropriate base such as, for example, an alkali metal carbonate or hydrogen carbonate, e.g., sodium carbonate, sodium hydrogen carbonate and the like; sodium hydride; or an organic base such as, for example, N,N-diethylethanamine or N-(1-methylethyl)-2-propanamine and/or the addition of an iodide salt, preferably an alkali metal iodide, may be appropriate. Somewhat elevated temperatures and stirring may enhance the rate of the reaction. A convenient alternative for reacting the intermediate of formula (IV) wherein —B—M represents —$NH_2$ with the reagents of formula (V) comprises stirring and heating the reactants in the presence of copper metal in a reaction-inert solvent such as described hereinbefore, in particular a dipolar aprotic solvent, e.g. N,N-dimethylformamide, N,N-dimethylacetamide and the like.

The compounds of formula (I) wherein B is —$NR^2$—, said compounds being represented by formula (I-b), can also be prepared by reacting an intermediate of formula (XII) with an intermediate of formula (VII) wherein B—M represents a radical —$NR^2$—H, said intermediate being represented by formula (VII-a), following art-known reductive N-alkylation procedures.

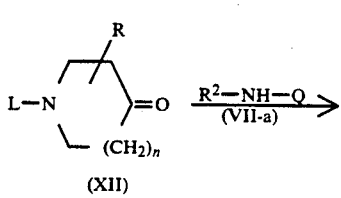

(XII)

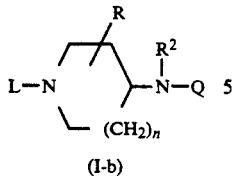
(I-b)

The reaction of (XII) with (VII-a) can conveniently be carried out by mixing the reactants in a suitable reaction-inert solvent with an appropriate reductant. Preferably, the ketone of formula (XII) is first reacted with the intermediate of formula (VII-a) to form an enamine, which optionally may be isolated and further purified, and subsequently reducing said enamine. Suitable solvents are, for example, water; $C_{1-6}$alkanols, e.g., methanol, ethanol, 2-propanol and the like; ethers, e.g., 1,4-dioxane and the like; halogenated hydrocarbons, e.g., trichloromethane and the like; dipolar aprotic solvents, e.g., N,N-dimethylformamide, N,N-dimethylacetamide, dimethylsulfoxide and the like; or a mixture of such solvents. Appropriate reductants are for example, metal or complex metal hydrides, e.g., sodium borohydride, sodium cyanoborohydride, lithium aluminum hydride and the like. Alternatively, hydrogen in the presence of a suitable catalyst such as, for example, palladium-on-charcoal, platinum-on-charcoal and the like may be used as reductant. In order to prevent the undesired further hydrogenation of certain functional groups in the reactants and the reaction products it may be advantageous to add an appropriate catalyst poison to the reaction mixture such as, for example, thiophene and the like.

The compounds of formula (I-b) wherein $R^2$ is H, said compounds being represented by formula (I-b-1), can also be prepared by a cyclodesulfurization reaction of an appropriate thiourea of formula (II-a) wherein $X^1$ is S, said thiourea being represented by formula (II-a-1), which may be formed in situ by condensing an isothiocyanate of formula (XIII) with a diamine of formula (III).

Said cyclodesulfurization reaction may be carried out by reacting (II-a-1) with an appropriate alkyl halide, preferably iodomethane, in a suitable reaction-inert organic solvent such as a $C_{1-6}$alkanol, e.g., methanol, ethanol, 2-propanol and the like. Alternatively, said cyclodesulfurization reaction may also be carried out by the reaction of (II-a-1) with an appropriate metal oxide or salt such as, for example, a Hg(II) or Pb(II) oxide or salt, e.g., HgO, HgCl$_2$, Hg(OAc)$_2$, PbO or Pb(OAc)$_2$ in an appropriate solvent following art-known procedures. In some instances it may be appropriate to supplement the reaction mixture with a small amount of sulfur. Also methanediimides, especially dicyclohexyl-carbodiimide may be used as cyclodesulfurizing agents.

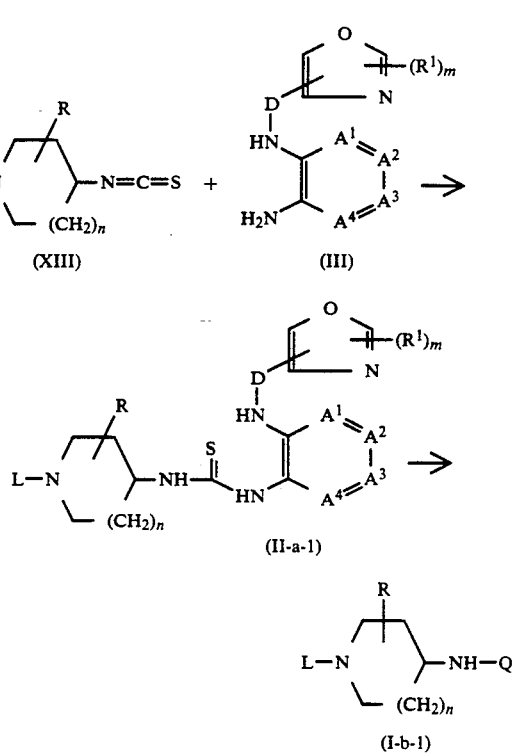

The compounds of formula (I) can also be prepared by N-alkylating an intermediate of formula (XV) with an appropriate alkylating reagent of formula (XIV).

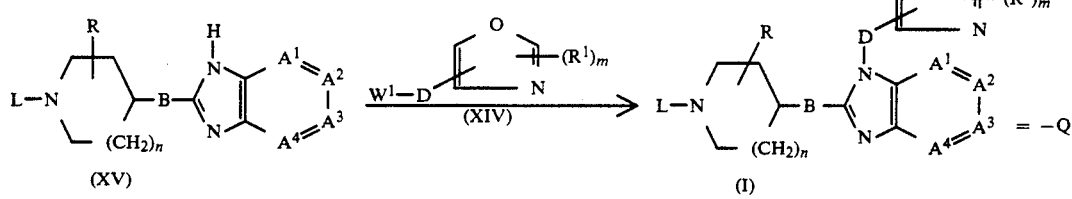

Said N-alkylation reaction can conveniently be conducted in a reaction-inert solvent such as, for example, water; an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethylsulfoxide, nitrobenzene, 1-methyl-2-pyrrolidinone and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Additionally, it may be advantageous to conduct said N-alkylation under an inert atmosphere such as, for example, oxygen-free argon or nitrogen.

Alternatively, said N-alkylation may be carried out by applying art-known conditions of phase transfer catalysis reactions. Said conditions comprise stirring the reactants with an appropriate base and optionally under an inert atmosphere as described hereinabove, in the presence of a suitable phase transfer catalyst such as, for example, a trialkylphenylmethylammonium, tetraalkylammonium, tetraalkylphosphonium, tetraarylphosphonium halide, hydroxide, hydrogen sulfur and the like catalysts.

The compounds of formula (I) wherein L is other than hydrogen, said L being represented by $L^1$, and said compounds being represented by formula (I-d) can also be prepared by N-alkylating a compound of formula (I) wherein L is hydrogen, said compound being represented by (I-e), with an alkylating reagent of formula (XVI).

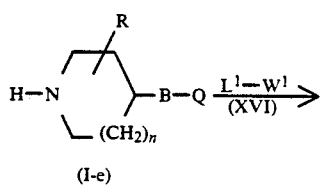

(I-e)

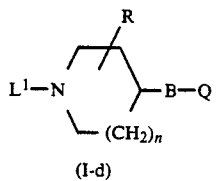

(I-d)

Said N-alkylation is conveniently conducted following art-known N-alkylation procedures as described hereinabove for the preparation of (I) from (XIV) and (XV).

The compounds of formula (I-d) wherein L is $C_{3-6}$cycloalkyl, $C_{1-12}$alkyl, a radical of formula (b-1), (b-2) or (b-3), said radicals being represented by the radical $L^2H—$ and said compounds by formula (I-d-1) can also be prepared by the reductive N-alkylation reaction of (I-e) with an appropriate ketone or aldehyde of formula $L^2=O$ (XVII), said $L^2=O$ being an intermediate of formula $L^2H_2$ wherein two germinal hydrogen atoms are replaced by $=O$, and $L^2$ is a germinal bivalent radical comprising $C_{3-6}$cycloalkylidene, $C_{1-12}$alkylidene, $R^3—C_{1-6}$alkyidene, $R^4—Y—C_{1-6}$alkylidene and $R^5—Z^2—C(=X)—Z^1—C_{1-6}$alkylidene.

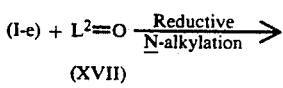

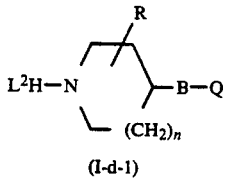

(I-d-1)

Said reductive N-alkylation can conveniently be carried out following the procedures described hereinabove for the preparation of compounds of formula (I-b) from (VII-a) and (XII), more particularly following the catalytic hydrogenation procedures.

The compounds of formula (I) wherein L is a radical formula (b-2) and $R^4$ is aryl or Het, said $R^4$ being represented by $R^{4-a}$ and said compounds by formula (I-d-2) may also be prepared by alkylating a compound of formula (I) wherein L is a radical of formula (b-2) and $R^4$ is hydrogen, said compound being represented by formula (I-d-3), with a reagent of formula (XVIII).

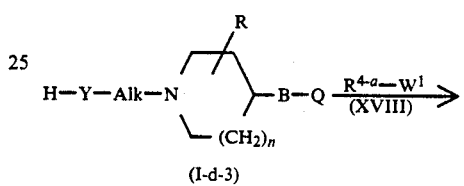

(I-d-3)

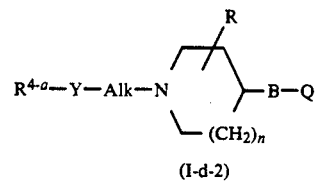

(I-d-2)

Similarly, the compounds of formula (I-d-2) may also be prepared by treating a compound of formula (I-d-4) with a reagent of formula (XIX).

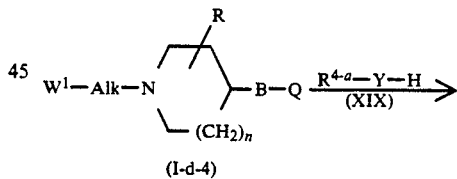

(I-d-4)

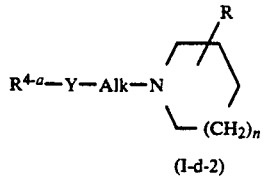

(I-d-2)

The alkylation reactions of (I-d-3) with (XVIII) and (I-d-4) with (XIX) may conveniently be conducted in an inert organic solvent such as, for example, an aromatic hydrocarbon, e.g., benzene, methylbenzene, dimethylbenzene; a ketone, e.g., 2-propanone, 4-methyl-2-pentanone; an ether, e.g., 1,4-dioxane, 1,1'-oxybisethane, tetrahydrofuran; and a dipolar aprotic solvent, e.g., N,N-dimethylformamide; N,N-dimethylacetamide; dimethyl sulfoxide; nitrobenzene; 1-methyl-2-pyurrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. Somewhat elevated temperatures may enhance the rate of the reaction.

The compounds of formula (I) wherein L is a radical of formula (b-3), $Z^1$ is NH, $Z^2$ is other than a direct bond and X is other than $NR^9$, said $Z^2$ and X being represented by $Z^{2-a}$ and $X^2$, and said compounds by (I-d-5), can be prepared by reacting an isocyanate ($X^2$=O) or isothiocyanate ($X^2$=S) of formula (XXI) with a reagent of formula (XX).

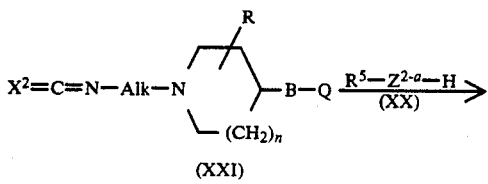

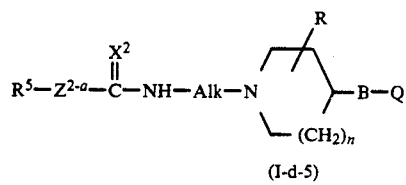

The compounds of formula (I) wherein L is a radical of formula (b-3), $Z^2$ is NH, $Z^1$ is other than a direct bond and X is other than $NR^9$, said $Z^1$ and X being represented by $Z^{1-a}$ and $X^2$, and said compounds by (I-d-6), can be prepared by reacting an isocyanate ($X^2$=O) or isothiocyante ($X^2$=S) of formula (XXII) with a compound of formula (I-d-7).

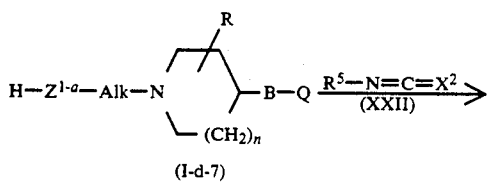

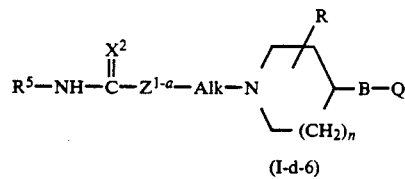

The reaction of (XX) with (XXI), or (XXII) with (I-d-7) can generally be conducted in a suitable reaction-inert solvent such as, for example, an ether, e.g., tetrahydrofuran and the like, a halogenated hydrocarbon, e.g., trichloromethane and the like. Elevated temperatures may be suitable to enhance the rate of the reaction.

The compounds of formula (I) wherein L is a radical of formula (b-3), $Z^2$ is a direct bond, $Z^1$ is other than a direct bond and X is other than $NR^9$, said $Z^1$ and X being represented by $Z^{1-a}$ and $X^2$, said compounds being represented by (I-d-8), can be prepared by reacting a reagent of formula (XXIII) or a reactive functional derivative thereof with a compound of formula (I-d-7).

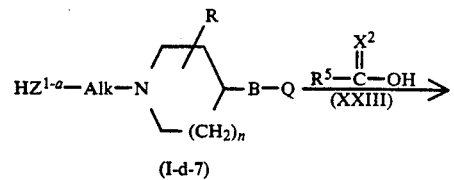

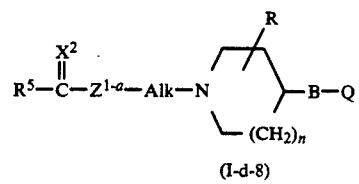

The reaction of (XXIII) with (I-d-7) may generally be conducted following art-known esterification or amidation reaction procedures. For example, the carboxylic acid may be converted into a reactive derivative, e.g., an anhydride or a carboxylic acid halide, which subsequently is reacted with (I-d-7); or by reacting (XXIII) and (I-d-7) with a suitable reagent capable of forming amides or esters, e.g., N,N-methanetetraylbis[cyclohexamine], 2-chloro-1-methylpyridinium iodide and the like. Said reactions may most conveniently be conducted in a suitable solvent such as, for example, an ether, e.g., tetrahydrofuran, a halogenated hydrocarbon, e.g., dichloromethane, trichloromethane, a dipolar aprotic solvent and the like. The addition of a base such as, for example, N,N-diethylethaneamine and the like may be appropriate.

The compounds of formula (I) wherein L is a radical of formula $L^3$—$C_{2-6}$alkanediyl, said $L^3$ being aryl, Het or a radical of formula $R^5$—$Z^2$—C(=X)—, and said compounds being represented by formula (I-d-9), may also be prepared by the addition reaction of a compound of formula (I-e) to an appropriate alkene of formula (XXIV).

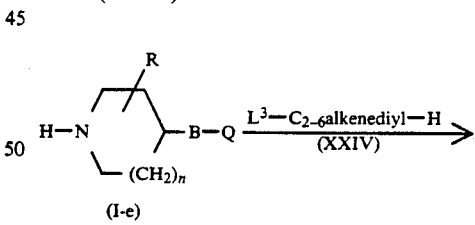

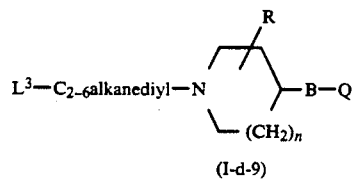

The compounds of formula (I) wherein L is 2-hydroxy-$C_{2-6}$alkyl or a radical of formula (b-4), said compounds being represented by formula (I-d-10), can be prepared by reacting a compound of formula (I-e) with an epoxide (XXV) wherein $R^{12}$ is hydrogen, $C_{1-4}$alkyl or a radical $R^6$—O—$CH_2$—.

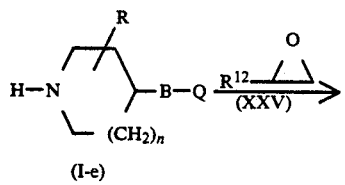

(I-e)

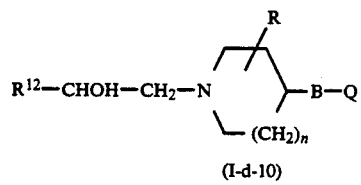

(I-d-10)

The reaction of (I-e) with respectively (XXIV) and (XXV) may be conducted by stirring and, if desired, heating the reactants in a reaction-inert solvent such as, for example, a ketone, e.g., 2-propanone, 4-methyl-2-pentanone, an ether, e.g., tetrahydrofuran, 1,1′-oxybisethane, an alcohol, e.g., methanol, ethanol, 1-butanol, a dipolar aprotic solvent, e.g., N,N-dimethylformamide, N,N-dimethylacetamide, and the like.

The compounds of formula (I) wherein $R^3$, $R^4$ or $R^5$ are Het, may also be prepared following art-known procedures for preparing heterocyclic ring systems or following analogous methods. A number of such cyclization procedures are described in for example, U.S. Pat. No. 4,695,575 and in the references cited therein, in particular U.S. Pat. Nos. 4,335,127; 4,342,870 and 4,443,451.

The compounds of formula (I) can also be converted into each other following art-known procedures of functional group transformation. Some examples of such procedures are cited hereinafter. The compounds of formula (I) containing a cyano substituent can be converted into the corresponding amines by stirring and, if desired, heating the starting cyano compounds in a hydrogen containing medium in the presence of an appropriate catalyst such as, for example, platinum-on-charcoal, Raney-nickel and the like catalysts. Suitable solvents are, for example, methanol, ethanol and the like. Amino groups may be alkylated or acylated following art-known procedures such as, for example, N-alkylation, N-acylation, reductive N-alkylation and the like methods. The compounds of formula (I) containing an amino group substituted with a radical arylmethyl, may be hydrogenolyzed by treating the starting compound with hydrogen in the presence of a suitable catalyst, e.g., palladium-on-charcoal, platinum-on-charcoal and the like, preferably in an alcoholic medium. The compounds of formula (I) wherein L is methyl or phenylmethyl can be converted into compounds of formula (I) wherein L is a $C_{1-6}$alkyloxycarbonyl group by reacting the methyl or phenylmethyl derivative with $C_{1-6}$alkyloxycarbonyl halides such as, for example, ethyl chloroformate in a suitable reaction-inert solvent and in the presence of a base like N,N-diethylethanamine. The compounds of formula (I) wherein L is hydrogen can be obtained from compounds of formula (I) wherein L is phenylmethyl or $C_{1-6}$alkyloxycarbonyl following art-known procedures like catalytic hydrogenation or hydrolysis in an acidic or alkaline medium depending on the nature of L.

In all of the foregoing and in the following preparations, the reaction products may be isolated from the reaction mixture and, if necessary, further purified according to methodologies generally known in the art.

Some intermediates and starting materials in the foregoing preparations are known compounds which may be prepared according to art-known methodologies of preparing said or similar compounds and other are new. A number of such preparation methods will be described hereinafter in more detail.

Starting materials such as the intermediates of formulae (II), (IV), (VI), (VIII), (X), (XII), (XIII) and (XV) can conveniently be prepared following procedures similar to those described in for example, U.S. Pat. Nos. 4,219,559; 4,556,660; 4,634,704; 4,695,569; 4,695,575, 4,588,722, 4,835,161 and 4,897,401 and in EP-A- 0,206,415; 0,282,133; 0,297,661 and 0,307,014.

The intermediates of formula (III) can be prepared from an aromatic starting material with vicinal halo and nitro substituents (XXVII) by reaction with a suitable amine of formula (XXVI), followed by art-known nitro-to-amine reduction.

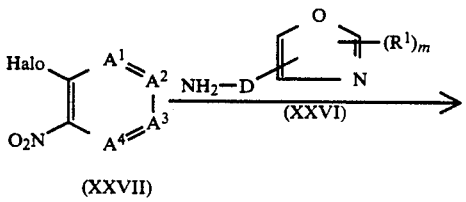

(XXVII)

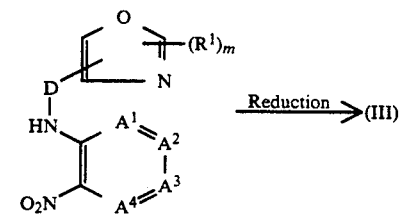

The intermediates of formulae (V), (VII), (IX) and (XI) then, can be prepared from the intermediates of formula (III) following art-known procedures of converting aromatic products with vicinal amino groups into benzimidazoles, imidazopyridines and/or purines.

The compounds of formula (I), the pharmaceutically acceptable acid addition salts and stereochemically isomeric forms thereof possess useful pharmacological properties. More particularly, they are active antiallergic and antihistaminic compounds which activity can clearly be demonstrated by, e.g., the results obtained in the test "Protection of Rats from Compound 48/80-induced lethality", the "PCA (passive cutane anaphylaxis)-test in Rats" described in Drug Dev. Res., 5, 137–145 (1985), the "Histamine-induced lethality test in Guinea Pigs" and the "Ascaris Allergy test in Dogs". The latter two tests are described in Arch. Int. Pharmacodyn. Ther. 251, 39–51 (1981).

The compounds of the present invention advantageously show a broad spectrum antiallergic profile, which can be evidenced by the excellent results obtained in the diversity of test procedures cited hereinbefore. As a second advantageous feature of the compounds of formula (I) there is the fact that they also have an attractive pharmacological profile adaptable to the continuously changing circumstances of antiallergic therapy. In particularly, they show a rapid onset of action and a particularly interesting duration of effect, neither too short nor too long.

In view of their antiallergic properties, the compounds of formula (I) and their acid addition salts are very useful in the treatment of broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) or a pharmaceutically acceptable acids addition salt form thereof.

Those of skill in treating allergic diseases in warm-blooded animals could easily determine the effective amount from the test results presented hereinafter. In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects. Unless otherwise stated all parts therein are by weight.

EXPERIMENTAL PART

A. PREPARATION OF THE INTERMEDIATES

EXAMPLE 1 a) To a suspension of 25.4 parts of 2-potassium-1H-isoindole-1,3(2H)-dione in 141 parts of N,N-dimethylformamide there was added dropwise a solution of 22 parts of 5-(bromomethyl)-2-methyloxazole in 141 parts of N,N-dimethylformamide. After stirring for 18 hours at room temperature, the reaction mixture was evaporated. The residue was partitioned between water and dichloromethane. The organic layer was separated, dried, filtered and evaporated. The residue was crystallized from acetonitrile in 2 fractions, yielding 24.2 parts (79.9%) of 2-[(2-methyl-5-oxazolyl)methyl]-1H-isoindole-1,3(2H)-dione (interm. 1).

b) A mixture of 12 parts of intermediate 1 and 100 ml of hydrochloric acid 7N was stirred for 4 hours at reflux temperature and for 18 hours at room temperature. The reaction mixture was filtered and the filtrate was concentrated. The residue was diluted with some water and basified with NaOH. The product was extracted with dichloromethane and the extract was dried, filtered and evaporated, yielding 4.3 parts (76.7%) of 2-methyl-5-oxazolemethanamine (interm. 2).

c) To a mixture of 5.95 parts of 2-chloro-3-nitropyridine, 79 parts of ethanol and 4.3 parts of intermediate 2 there were added 3.78 parts of sodium hydrogen carbonate. After stirring for 6 hours at reflux temperature, the reaction mixture was evaporated. The residue was partitioned between dichloromethane and water. The organic layer was separated, dried, filtered and evaporated. The residue was co-evaporated with methylbenzene, yielding 8.4 parts (95.6%) of N-[2-methyl-5-oxazolyl)methyl]-3-nitro-2-pyridinamine (interm. 3).

d) A mixture of 8.4 parts of intermediate 3, 2 parts of a solution of thiophene in methanol 4% and 198 parts of methanol was hydrogenated at normal pressure and room temperature in the presence of 2 parts of palladium-on-charcoal catalyst 10%. After the calculated amount of hydrogen was taken up, the catalyst was filtered off and the filtrate was evaporated, yielding 7.6 parts (100%) of $N^2$-[(2-methyl-5-oxazolyl)methyl]-2,3-pyridinediamine (interm. 4).

e) A mixture of 7.64 parts of intermediate 4, 165 parts of tetrahydrofuran, 8.04 parts of ethyl 4-isothiocyanato-1-piperidinecarboxylate and 94 parts of N,N-dimethylformamide was stirred for 20 hours at 50° C. The reaction mixture was used as such for further synthesis. Theoretical yield: 15.7 parts (100%) of ethyl 4-[[[2-[[(2-methyl-5-oxazolyl)methyl]amino]-3-pyridinyl]amino]- thioxomethyl]amino]-1-piperidinecarboxylate (interm. 5).

In a similar manner there were also prepared:
ethyl 4-[[[[4-[[(2-methyl-5-oxazolyl)methyl]amino]-3-pyridinyl]amino]thioxomethyl]amino]-1-piperidinecarboxylate (interm. 6),
ethyl 4-[[[[4-[[(2-methyl-5-oxazolyl)methyl]amino]-5-pyrimidinyl]amino]thioxomethyl]amino]-1-piperidinecarboxylate (interm. 7) and
ethyl 4-[[[[3-[[(2-methyl-5-oxazolyl)methyl]amino]-4-pyridinyl]amino]thioxomethyl]amino]-1-piperidinecarboxylate (interm. 8).

EXAMPLE 2 a) To a mixture of 795 parts of dry tetrachloromethane, 40.1 parts of N-bromosuccinimide and a view parts of benzoylperoxide there were added 25 parts of 2,4,5-trimethyloxazole under a nitrogen atmosphere. The whole was stirred for 1 hour at reflux temperature. After cooling in an ice/salt bath, the reaction mixture was filtered and the filtrate was evaporated, yielding 42.7 parts (99.9%) of 5-bromomethyl)-2,4-dimethyloxazole (interm. 9).

b) To a mixture of 43 parts of intermediate 9 in 423 parts of N,N-dimethylformamide there were added portionwise 23.75 parts of N-formyl-N-sodiumformamide. After stirring for 1 hour at 50° C. and for 18 hours at room temperature, the reaction mixture was evaporated, yielding 41 parts (100%) of N-[(2,4-dimethyl-5-oxazolyl)methyl]-N-formylformamide (interm. 10).

c) A mixture of 41 parts of intermediate 10, 152 parts of hydrochloric acid (conc.) and 395 parts of ethanol was stirred for 1 hour at reflux temperature and for 18 hours at room temperature. The reaction mixture was filtered and the precipitate was washed with ethanol. The combined filtrates were evaporated and the residue was taken up in ice-water. After basifying with NaOH (aq.), the product was extracted with dichloromethane. The extract was dried, filtered and evaporated, yielding 28 parts (98.6%) of 2,4-dimethyl-5-oxazolemethanamine (interm. 11).

d) A mixture of 28 parts of intermediate 11, 395 parts of ethanol, 37.7 parts of 2-chloro-3-nitropyridine and 23.85 parts of sodium carbonate was stirred for 6 hours at reflux temperature. The reaction mixture was evaporated and the residue was taken up in water. The product was extracted with dichloromethane and the extract was dried, filtered and evaporated. The residue was purified by column chromatography (HPLC; silica gel; hexane/$CH_3COOC_2H_5$ 60:40). The eluent of the desired fraction was evaporated, yielding 27 parts (48.3%) of N-[(2,4-dimethyl-5-oxazolyl)methyl]-3-nitro-2-pyridinamine (interm. 12).

e) A mixture of 26.5 parts of intermediate 12, 3 parts of a solution of thiophene in methanol 4% and 316 parts of methanol was hydrogenated at normal pressure and room temperature in the presence of 4 parts of platinum-on-charcoal catalyst 5%. After the calculated amount of hydrogen was taken up, the catalyst was filtered off and the filtrate was evaporated, yielding 21.8 parts (100%) of $N^2$-[(2,4-dimethyl-5-oxazolyl)methyl]-2,3-pyridinediamine (interm. 13).

EXAMPLE 3

To a solution of 33.63 parts of 1-amino-4-methoxy-2-nitrobenzene in 282 parts of N,N-dimethylformamide there were added 21.2 parts of sodium carbonate and a solution of 35.2 parts of 5-bromomethyl-2-methyloxazole in 94 parts of N,N-dimethylformamide. The whole was stirred for 20 hours at 70° C. and was then evaporated. The residue was taken up in water and the product was extracted with dichloromethane. The extract was dried, filtered and evaporated. The residue was purified by column chromatography (silica gel; $CH_2C_2/CH_3OH$ 95:5). The eluent of the desired fraction was evaporated and the residue was crystallized from petroleum ether. The product was filtered off and dried, yielding 30 parts (57.0%) of N-(4-methoxy-2-nitrophenyl)-2-methyl-5-oxazolemethanamine (interm. 14).

Following the procedure of Example 1 (d) and (e), intermediate 14 was converted into ethyl 4-[[[[5-methoxy-2-[[(2-methyl-5-oxazolyl)methyl]amino]phenyl]amino]thioxomethyl]amino]-1-piperidinecarboxylate (interm. 15).

EXAMPLE 4 a) To a stirred mixture of 412 parts of N,N'-methanetetraylbis[cyclohexanamine] and 2225 parts of tetrahydrofuran there were added dropwise 1092 parts of carbon disulfide and, after cooling to −10° C., portionwise 228 parts of 1-methyl-4-piperidinamine. The whole was stirred for 1 hour at room temperature and was then evaporated. The residue was recrystallized from 2,2'-oxybispropane. The product was filtered off and dried, yielding 416.6 parts (100%) of 4-isothiocyanato-1-methylpiperidine (interm. 16).

b) To a mixture of 28 parts of intermediate 11 in 395 parts of ethanol there were added 37.7 parts of 2-chloro-3-nitropyridine and 23.85 parts of sodium carbonate. After stirring for 6 hours at reflux temperature, the reaction mixture was evaporated. The residue was taken up in water and the product was extracted with dichloromethane. The extract was dried, filtered and evaporated and the residue was purified by column chromatography (silica gel; hexane/$CH_3COOC_2H_5$ 60:40). The eluent of the desired fractions was evaporated, yielding 27 parts (48.3%) of N-[(2,5-dimethyl-4-oxazolyl)methyl]-3-nitro-2-pyridinamine (interm. 17).

Following the procedure of Example 1(d) and (e), intermediate 17 was converted into N-[2-[[(2,5-dimethyl-4-oxazolyl)methyl]amino]-3-pyridinyl]-N'-(1-methyl-4-piperidinyl)thiourea (interm. 18).

In a similar manner there were also prepared:
N-[4-methoxy-2-[[(2-methyl-5-oxazolyl)methyl]amino]phenyl]-N'-(1-methyl-4-piperidinyl)thiourea (interm. 19) and
N-[4-fluoro-2-[[(2-methyl-5-oxazolyl)methyl]amino]phenyl]-N'-(1-methyl-4-piperidinyl)thiourea (interm. 20).

EXAMPLE 5 a) To a mixture of 6.2 parts of ethyl 5-methyl-2-oxazolecarboxylate and 191 parts of dry tetrachloromethane there were added 7.1 parts of N-bromosuccinimide and a few parts of benzoylperoxide under a nitrogen atmosphere. The whole was stirred for 1 hour at reflux temperature. After cooling, the reaction mixture was filtered and the filtrate was evaporated, yielding 11 parts (100%) of ethyl 5-(bromomethyl)-2-oxazolecarboxylate (interm. 21).

b) To a mixture of 11.52 parts of ethyl 4-[(1H-benzimidazol-2-yl)amino]-1-piperidinecarboxylate and 235 parts of N,N-dimethylformamide there were added portionwise 1.92 parts of a dispersion of sodium hydride in mineral oil (50%). After stirring for ½ hour, there was added dropwise a solution of 11 parts of intermediate 21 in 47 parts of N,N-dimethylformamide, while cooling on ice. The whole was stirred for 18 hours while slowly warming to room temperature. The reaction mixture was evaporated and the residue was partitioned between water and 4-methyl-2-pentanone. The organic layer was dried, filtered and evaporated and the residue was purified by column chromatography (silica gel; $CH_2Cl_2/CH_3OH$ 95:5). The eluent of the desired fraction was evaporated and the residue was successively crystallized from 2,2'-oxybispropane and acetonitrile. The product was filtered off and dried, yielding 10 parts (56.6%) of ethyl 4-[[1-[[2-(ethoxycarbonyl)-5-oxazolyl]-methyl]-1H-benzimidazol-2-yl]amino]-1-piperidinecarboxylate; mp. 132.1° C. (interm. 22).

In a similar manner there was also prepared:

1,1-dimethylethyl 4-[[1-[[2-(ethoxycarbonyl)-5-oxazolyl]methyl]-1H-benzimidazol-2-yl]amino]-1-piperidinecarboxylate; mp. 199.8° C. (interm. 23).

EXAMPLE 6 a) To a mixture of 38.1 parts of 2-chloro-1H-benzimidazole and 235 parts of N,N-dimethylformamide there were added 44 parts of 5-bromomethyl-2-methyloxazole, 26.5 parts of sodium carbonate and a few crystals of potassium iodide. After stirring for 18 hours at 70° C., the reaction mixture was evaporated and the residue was partitioned between water and dichloromethane. The organic layer was separated, dried, filtered and evaporated. The residue was crystallized from 2,2'-oxybispropane (2×), yielding 9.01 parts (14.6%) of product. Evaporation of the combined mother liquors yielded an additional 10.23 parts (16.5%) of product. Total yield: 19.24 parts (31.1%) of 2-chloro-1-[(2-methyl-5-oxazolyl)methyl]-1H-benzimidazole; mp. 101.0° C. (interm. 24).

b) A mixture of 14.73 parts of intermediate 24, 5.03 parts of thiourea and 79 parts of ethanol was stirred for 4 hours at reflux temperature. The reaction mixture was evaporated and the residue was purified by column chromatography (silica gel; $CH_2Cl_2/CH_3OH$ 98:2). The eluent of the desired fraction was evaporated and the residue was crystallized from acetonitrile. The product was filtered off and dried, yielding 19.33 parts (99.0%) of 1-[(2-methyl-5-oxazolyl)methyl]-1H-benzimidazole-2-thiol; mp. 153.3° C. (interm. 25).

EXAMPLE 7

To a solution of 18.5 parts of 2,5-dimethyl-4-oxazolemethanol in 200 parts of trichloromethane there were added dropwise 21.1 parts of thionyl chloride. After stirring for 2 hours at room temperature, the reaction mixture was evaporated and the residue was co-evaporated with methylbenzene, yielding 26.4 parts (100%) of 4-(chloromethyl)-2,5-dimethyloxazole hydrochloride (interm. 26).

EXAMPLE 8

To a stirred mixture of 2.5 parts of sodium tetrahydroborate and 87 parts of 1,2-dimethoxyethane there were added 2.82 parts of lithium chloride and, after 1 hour, dropwise 15.5 parts of ethyl 2-methyl-4-oxazolecarboxylate. Stirring was continued for 10 hours at 95° C. and for 18 hours at room temperature. There were added ethyl acetate and some water and the whole was poured into 120 parts of ice-water acidified with 15 parts of HCl. The aqueous layer was separated and successively extracted with 2,2'-oxybispropane, basified with NaOH and extracted with dichloromethane. The latter extract was dried, filtered and evaporated. The residue was distilled (133 Pa, 75° C.), yielding 3.7 parts (32.7%) of 2-methyl-4-oxazolemethanol (interm. 27).

b) To a solution of 3.7 parts of intermediate 27 in 133 parts of dichloromethane there were added 4.1 parts of N,N-diethylethanamine and dropwise 4.14 parts of methanesulfonyl chloride, while cooling on ice. Stirring and cooling was continued for 2 hours. At room temperature, the reaction mixture was diluted with water. The organic layer was separated, washed with water, dried, filtered and evaporated. The residue was co-evaporated with methylbenzene, yielding 5 parts (79.2%) of 2-methyl-4-oxzolemethanol methanesulfonate (ester) (interm. 28).

In a similar manner there were also prepared:

5-methyl-2-oxazolemethanol methanesulfonate(ester) (interm. 29) and 5-methyl-4-oxazolemethanol methanesulfonate(ester) (interm. 30).

B. PREPARATION OF THE FINAL COMPOUNDS

EXAMPLE 9

A mixture of 23 parts of 5-(bromomethyl)-2-methyloxazole, 57.6 parts of ethyl 4-[(1H-benzimidazol-2-yl)amino]-1-piperidinecarboxylate, 26.5 parts of sodium carbonate and 470 parts of N,N-dimethylformamide was stirred for 18 hours at 80° C. The reaction mixture was poured into water and the whole was extracted with 4-methyl-2-pentanone. The extract was washed with water, dried, filtered and evaporated. The residue was stirred in acetonitrile. The precipitate was filtered off and the filtrate was evaporated. The residue was purified by column chromatography (silica gel; $CH_2Cl_2/CH_3OH$ 90:10). The eluent of the desired fraction was evaporated, yielding 6 parts (11.2%) of ethyl 4-[[1-[(2-methyl-5-oxazolyl)methyl]-1H-benzimidazol-2-yl]amino]-1-piperidinecarboxylate (comp. 2).

EXAMPLE 10

To a solution of 26 parts of 2-[[1-(phenylmethyl)-4-piperidinyl]methyl]-1H-benzimidazole in 282 parts of N,N-dimethylformamide there were added 4.8 parts of a dispersion of sodium hydride in mineral oil (50%) under a nitrogen atmosphere. After stirring for 1 hour, there was added portionwise a solution of 15 parts of 5-(bromomethyl)-2-methyloxazole in 47 parts of N,N-dimethylformamide, while cooling in an ice-bath (<20° C.). The whole was stirred for 18 hours and allowed to warm to room temperature. The oily layer was separated and discarded. The N,N-dimethylformamide layer was poured into water and the whole was extracted with 4-methyl-2-pentanone (3×). The combined extracts were washed with water, dried, filtered and evaporated. The residue was purified by column chromatography (silica gel; $CH_2Cl_2/CH_3OH$ 90:10). The eluent of the desired fraction was evaporated and the residue was successively crystallized from 2,2'-oxybispropane and acetonitrile, yielding 14.31 parts (42.0%) of 1-[(2-methyl-5-oxazolyl)methyl]-2-[[1-(phenylmethyl)-4-piperidinyl]methyl]-1H-benzimidazole; mp. 108.6° C. (comp. 1).

EXAMPLE 11

A mixture of 15.7 parts of intermediate (5), 94 parts of N,N-dimethyl-formamide, 10.2 parts of mercury(II)oxide and a few parts of sulfur was stirred for 3 hours at 75° C. The reaction mixture was filtered over diatomaceous earth and the latter was rinsed with N,N-dimethylformamide till colorless. The combined filtrates were evaporated and the residue was partitioned between water and dichloromethane. The organic layer was separated, dried, filtered and evaporated. The residue was purified by column chromatography (silica gel; $CH_2Cl_2/CH_3OH$ 90:10). The eluent of the desired fraction was evaporated, yielding 5.5 parts (38.2%) of ethyl 4-[[3-[(2-methyl-5-oxazolyl)methyl]-3H-imidazo[4,5-b]pyridin-2-yl]amino]-1-piperidine-carboxylate (comp. 94).

EXAMPLE 12

To a solution of 21.8 parts of intermediate (13) in 235 parts of N,N-dimethylformamide there were added 21.4 parts of ethyl 4-isothiocyanato-1-piperidinecarboxylate and, after stirring for 20 hours at 50° C., 27.1 parts of mercury(II)oxide and a few parts of sulfur. Stirring was continued for 3½ hours at 75° C. The reaction mixture was filtered over diatomaceous earth and the filtrate was evaporated. The residue was partitioned between water and dichloromethane. The organic layer was separated, dried, filtered and evaporated. The residue was purified by column chromatography (silica gel; $CH_2Cl_2/CH_3OH$ 95:5). The eluent of the desired fraction was evaporated and the residue was successively crystallized from 2,2'-oxybis-propane and acetonitrile. The product was filtered off and dried, yielding 16.62 parts (41.7%) of ethyl 4-[[3-[(2,4-dimethyl-5-oxazolyl)-methyl]-3H-imidazo[4,5-b]pyridin-2-yl]amino]-1-piperidinecarboxylate (comp. 153).

EXAMPLE 13

To a solution of 12.97 parts of ethyl 4-hydroxy-1-piperidinecarboxylate in 705 parts of N,N-dimetylformamide there were added 3.6 parts of a dispersion of sodium hydride in mineral oil (50%) under a nitrogen atmosphere. The whole was stirred for ½ hour at room temperature and for ½ hour at 40° C. After cooling, there were added 18.6 parts of intermediate 24, keeping the temperature below 20° C. Stirring was continued for 18 hours. The reaction mixture was evaporated and the residue was partitioned between water and dichloromethane. The organic layer was separated, dried, filtered and evaporated. The residue was treated with activated charcoal in methanol. After filtration, the whole was evaporated and the residue was purified by column chromatography (silica gel; $CH_2Cl_2/CH_3OH$ 98:2). The eluent of the desired fractions was evaporated, yielding 23.5 parts (81.5%) of ethyl 4-[[1-[(2-methyl-5-oxazolyl)-methyl]-1H-benzimidazol-2-yl]oxy]-1-piperidine-carboxylate (comp. 63).

EXAMPLE 14 a) The following reaction was carried out under a nitrogen atmosphere. To a mixture of 8.8 parts of intermediate (25) in 188 parts of N,N-dimethylformamide there were added 1.92 parts of a dispersion of sodium hydride in mineral oil (50%) and, after stirring for 1½ hour at room temperature, 13.33 parts of 1-[(4-methylphenyl)sulfonyl]-4-piperidinol methanesulfonate(ester). The whole was stirred for 18 hours and then evaporated. The residue was partitioned between water and dichloromethane. The organic layer was separated, dried, filtered and evaporated. The residue was purified by column chromatography (silica gel; $CH_2Cl_2/CH_3OH$ 98:2). The eluent of the desired fraction was evaporated, yielding 12.4 parts (71.4%) of 4-[[1-[(2-methyl-5-oxazolyl)methyl]-1H-benzimidazol-2-yl]thio]-1-[(4-methylphenyl)sulfonyl]piperidine (interm. 31).

b) A mixture of 10 parts of intermediate (31) and 149 parts of hydrobromic acid (48%) was stirred for 3 hours at reflux temperature. The reaction mixture was evaporated and the residue was taken up in water. The whole was basified with NaOH (aq.) and then extracted with dichloromethane. The extract was dried, filtered and evaporated. The residue was purified by column chromatography (silica gel; $CH_2Cl_2/CH_3OH(NH_3)$ 90:10). The eluent of the desired fraction was evaporated and the residue was converted into the cyclohexylsulfamate (1:2) salt in 2-propanone. The salt was filtered off and dried, yielding 8.85 parts (53.7%) of 1-[(2-methyl-5-oxazolyl)methyl]-2-(4-piperidinylthio)-1H-benzimidazole cyclohexylsulfamate (1:2); mp. 147.8° C. (comp. 85).

EXAMPLE 15 a) To a mixture of 4.7 parts of intermediate (23) and 89 parts of tetrahydrofuran there were added 3.5 ml of a solution of lithium tetrahydroborate in tetrahydrofuran 2M under a nitrogen atmosphere. The whole was stirred for 10 hours at reflux temperature and for 24 hours at room temperature. After cooling on ice, there were added ethyl acetate and some water. The organic layer was separated, dried, filtered and evaporated. The residue was successively crystallized from 2,2'-oxybis-propane and acetonitrile, yielding 0.92 parts (21.5%) of 1,1-dimethylethyl 4-[[1-[[2-(hydroxymethyl)-5-oxazolyl]methyl]-1H-benzimidazol-2-yl]amino]-1-piperidinecarboxylate (comp. 141); mp. 132.3° C.

b) A mixture of 8.3 parts of compound (141), 133 parts of 2-propanol saturated with HCl and 13.4 parts of methanol was refluxed for 1½ hour. The reaction mixture was evaporated and the residue was crystallized from 2-propanol. The product was filtered off and dried, yielding 6.1 parts (72.0%) of 5-[[2-(4-piperidinylamino)-1H-benzimidazol-1-yl]methyl]-2-oxazolemethanol trihydrochloride hemihydrate; mp. 279.5° C. (comp. 146).

c) A mixture of 3.4 parts of 1-(2-chloroethyl)-4-methoxybenzene, 5.2 parts of compound (146), 3.2 parts of sodium carbonate, a few crystals of potassium iodide and 160 parts of 4-methyl-2-pentanone was refluxed for 48 hours. The reaction mixture was evaporated and the residue was taken up in water. The product was extracted with dichloromethane and the extract was dried, filtered and evaporated. The residue was crystallized from acetonitrile, yielding 1.24 parts (19.9%) of 5-[[2-[[1-[2-(4-methoxyphenyl)ethyl]-4-piperidinyl]amino]-1H-benzimidazol-1-yl]methyl]-2-oxazolemethanol monohydrate; mp. 130.7° C. (comp. 147).

EXAMPLE 16

A mixture of 6 parts of compound (2) 10.22 parts of potassium hydroxide and 66.3 parts of 2-propanol was stirred for 6 hours at reflux temperature and for 18 hours at room temperature. The reaction mixture was evaporated and the residue was co-evaporated with water and then partitioned between a small amount of water and dichloro-methane. The organic layer was separated, dried, filtered and evaporated. The residue was purified by column chromatography (silica gel; $CH_2Cl_2/CH_3OH(NH_3)$ 85:15). The eluent of the desired fraction was evaporated and the residue was crystallized from acetonitrile in two fractions, yielding 2.21 parts (45.4%) of 1-[(2-methyl-5-oxazolyl)-methyl]-N-(4-piperidinyl)-1H-benzimidazol-2-amine; mp. 227.2° C. (comp. 3).

EXAMPLE 17

A mixture of 3.1 parts of compound (3) 1 part of polyoxymethylene, 2 parts of a solution of thiophene in methanol 4% and 119 parts of methanol was hydrogenated at normal pressure and room temperature in the presence of 2 parts of platinum-on-charcoal catalyst 5%. After the calculated amount of hydrogen was taken up, the catalyst was filtered off and the filtrate was evaporated. The residue was purified by column chromatography (silica gel; $CH_2Cl_2/CH_3OH(NH_3)$ 95:5). The eluent of the desired fraction was evaporated and the residue was crystallized from acetonitrile. The product was filtered off and dried, yielding 0.82 parts (24.5%) of 1-[(2-methyl-5-oxazolyl)methyl]-N-(1-methyl-4-piperidinyl)-1H-benzimidazol-2-amine hemihydrate; mp. 78.2° C. (comp. 9).

EXAMPLE 18

A mixture of 2.6 parts of 6-(2-chloroethyl)-7-methyl-5H-thiazolo[3,2-a]pyrimidin-5-one monohydrochloride, 3.1 parts of compound (5), 2.1 parts of sodium carbonate and 160 parts of 4-methyl-2-pentanone was refluxed for 18 hours. The reaction mixture was evaporated and the residue was taken up in water. The product was extracted with dichloromethane and the extract was dried, filtered and evaporated. The residue was purified by column chromatography (silica gel; $CH_2Cl_2/CH_3OH(NH_3)$ 95:5). The eluent of the desired fraction was evaporated and the residue was crystallized from acetonitrile. The product was filtered off and dried, yielding 1.34 parts (26.7%) of 7-methyl-6-[2-[4-[[1-[(2-methyl-5-oxazolyl)methyl]-1H-benzimidazol-2-yl]methyl]-1-piperidinyl]ethyl]-5H-thiazolo[3,2-a]pyrimidin-5-one; mp. 173.8° C. (comp. 14).

EXAMPLE 19 a) To a stirred mixture of 11.0 parts of compound (5), 6.0 parts of triethylamine and 122 parts of N,N-dimethylformamide there was added dropwise a solution of 3.6 parts of chloroacetonitrile in 19 parts of N,N-dimethylformamide. Stirring at room temperature was continued for 36 hours. The reaction mixture was poured into a saturated NaCl solution and the whole was extracted with a mixture of ethyl acetate and 4-methyl-2-pentanone (1:1). The organic layer was separated, washed with water, dried, filtered and evaporated. The residue was converted into the (E)-2-butene-dioate (2:3) salt in 2-propanol, yielding 13.75 parts (72.9%) of 4-[[1-[(2-methyl-5-oxazolyl)methyl]-1H-benzimidazol-2-yl]methyl]-1-piperidineacetonitrile (E)-2-butanedioate (2:3), mp. 189.6° C. (comp. 18).

b) A mixture of 10 parts of compound (18) and 237 parts of methanol saturated with ammonia was hydrogenated at normal pressure and room temperature in the presence of 3 parts of Raney nickel. After the calculated amount of hydrogen was taken up, the catalyst was filtered off and the filtrate was evaporated, yielding 9.6 parts (90.5%) of 4-[[1-[(2-methyl-5-oxazolyl)methyl]-1H-benzimidazol-2-yl]methyl]-1-piperidineethanamine (comp. 19).

c) A mixture of 1.1 parts of 2-chloropyrimidine, 3.2 parts of compound (19), 1.7 parts of sodium hydrogen carbonate and 119 parts of ethanol was stirred for 20 hours at reflux temperature. After cooling, the reaction was filtered over diatomaceous earth. The filtrate was evaporated and the residue was purified by column chromatography (silica gel; $CH_2Cl_2/CH_3OH(NH_3)$ 98:2→96.4). The eluent of the desired fraction was evaporated and the residue was converted into the ethanedioate (1:2) salt in ethanol. The salt was recrystallized from ethanol, yielding 2.7 parts (49.1%) of N-[2-[4-[[1-[(2-methyl-5-oxazolyl)methyl]-1H-benzimidazol-2-yl]methyl]-1-piperidinyl]ethyl]-2-pyrimidinamine ethanedioate (1:2); mp. 173.7° C. (comp. 20).

EXAMPLE 20

A mixture of 2.2 parts of 2-ethenylpyridine, 3.1 parts of compound (3) and 81 parts of 1-butanol was stirred for 44 hours at reflux temperature. After cooling, the reaction mixture was evaporated. The residue was purified by column chromatography (silica gel; $CH_2Cl_2/CH_3OH(NH_3)$ 97:3). The eluent of the desired fraction was evaporated and the residue was converted into the (E)-2-butenedioate (1:1) salt in ethanol. The salt was successively recrystallized from a mixture of 4-methyl-2-pentanone and ethanol and from 2-propanol, yielding 1.1 parts (20.6%) of 1-[(2-methyl-5-oxazolyl)methyl]-N-[1-[2-(2-pyridinyl)ethyl]-4-piperidinyl]-1H-benzimidazol-2-amine (E)-2-butenedioate (1:1); mp. 184.6° C. (comp. 21).

EXAMPLE 21 a) A mixture of 6.2 parts of compound (3) and 119 parts of methanol was stirred for 15 min while oxirane was bubbled through. Stirring was continued for 3 hours during which period oxirane was bubbled through for another 15 min. The reaction mixture was evaporated and the residue was purified by column chromatography (silica gel; $CH_2Cl_2/CH_3OH(NH_3)$ 95:5). The eluent of the desired fraction was evaporated and the residue was converted into the (E)-2-butenedioate (1:2) salt in 2-propanol. The salt was successively recrystallized from a mixture of 2-propanol and ethanol and from 2-propanol, yielding 4.06 parts (31.3%) of 4-[[1-[(2-methyl-5-oxazolyl)methyl]-1H-benzimidazol-2-yl]amino]-1-piperdineethanol (E)-2-butenedioate (1:2) 2-propanolate (1:1); mp. 201.2° C. (comp. 36).

b) To a stirred mixture of 3.6 parts of compound (36), 1.2 parts of 2-[di-(2-hydroxyethyl)amino]ethanol and 106.4 parts of dichloromethane there was added dropwise a solution of 13 parts of methanesulfonyl chloride in 26.6 parts of dichloromethane under a nitrogen atmosphere. Stirring at room temperature was continued for 18 hours. The reaction mixture was washed with water (2×), dried, filtered and evaporated, yielding 3.6 parts (100%) of 2-[4-[[1-[(2-methyl-5-oxazolyl)methyl]-1H-benzimidazol-2-yl]amino]-1-piperidinyl]ethyl methanesulfonate (ester) (interm. 32).

c) A mixture of 1.1 parts of 1-methyl-1H-imidazole-2-thiol, 3.5 parts of intermediate (32), 1.4 parts of potassium carbonate and 119 parts of 2-propanone was stirred for 12 hours at reflux temperature. The reaction mixture was evaporated and the residue was partitioned between water and dichloromethane. The organic layer was separated, dried, filtered and evaporated. The residue was purified by column chromatography (silica gel; $CH_2Cl_2/CH_3OH$ 95:5). The eluent of the desired fraction was evaporated and the residue was converted into the ethanedioate (1:3) salt in ethanol. The salt was recrystallized from ethanol, yielding 1.0 part (17.1%) of N-[1-[2-[(1-methyl-1H-imidazol-2-yl)thio]ethyl]-4-piperidinyl]-1-[(2-methyl-5-oxazolyl)methyl]-1H-benzimidazol-2-amine ethanedioate (1:3) hemihydrate; mp. 195.2° C. (comp. 68).

EXAMPLE 22

A mixture of 0.7 parts of isocyanatomethane, 3.5 parts of compound (30) and 134 parts of tetrahydrofuran was stirred for 18 hours at room temperature. The reaction mixture was evaporated and the residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried, yielding 2.8 parts, (68.0%) of N-methyl-N'-[2-[4-[[1-[(2-methyl-5-oxazolyl)methyl]-1H-benzimidazol-2-yl]amino]-1-piperidinyl]ethyl]urea; mp. 203.4° C. (comp. 31).

EXAMPLE 23

To a stirred mixture of 2.1 parts of 3-amino-2-pyrazinecarboxylic acid, 2.8 parts of 2-chloro-1-methylpyridinium iodide and 266 parts of dichloromethane there were added 1.5 parts of N,N-diethylethanamine and, after 15 min, 4.6 parts of compound (30). Stirring at room temperature was continued for 1 hour. The reaction mixture was washed with water, dried, filtered and evaporated. The residue was purified by column chromatography (silica gel; CH$_2$Cl$_2$/CH$_3$OH(NH$_3$) 95:5). The eluent of the desired fraction was evaporated and the residue was crystallized from acetonitrile. The product was filtered off and dried, yielding 1.79 parts (24.2%) of 3-amino-N-[2-[4-[[1-[(2-methyl-5-oxazolyl)methyl]-1H-benzimidazol-2-yl]amino]-1-piperidinyl]ethyl]-2-pyrazinecarboxamide monohydrate; mp. 134.2° C. (comp. 42).

EXAMPLE 24

A mixture of 2.3 parts of 1-methyl-1H-indol-2-carbonyl chloride, 3.5 parts of compound (30), 3 parts of N,N-diethylethanamine and 298 parts of trichloromethane was stirred for 18 hours at room temperature. The reaction mixture was washed with water, dried, filtered and evaporated. The residue was purified by column chromatography (silica gel; CH$_2$Cl$_2$/CH$_3$OH(NH$_3$) 95:5). The eluent of the desired fraction was evaporated and the residue was crystallized from 2,2'-oxybispropane. The product was filtered off and dried, yielding 0.61 part (11.9%) of 1-methyl-N-[2-[4-[[1-[(2-methyl-5-oxazolyl)methyl]-1H-benzimidazol-2-yl]amino]-1-piperidinyl]ethyl]-1H-indole-2-carboxyamide; mp. 104.0° C. (comp. 65).

EXAMPLE 25

To a stirred and heated (60° C.) mixture of 1.6 parts of 2H-3,1-benzoxazine-2,4(1H)-dione and 37.6 parts of N,N-dimethylformamide there was added dropwise a solution of 3.5 parts of compound (30) in 28.2 parts of N,N-dimetylformamide. Stirring was continued for 4 hours at 60° C. and for 18 hours at room temperature. The reaction mixture was poured into water and the product was extracted with a mixture of 4-methyl-2-pentanone and ethyl acetate (1:1) (3×). The combined extracts were washed with NaCl (aq.), dried, filtered and evaporated. The residue was purified by column chromatography (silica gel; CH$_2$Cl$_2$/CH$_3$OH(NH$_3$) 95:5). The eluent of the desired fraction was evaporated and the residue was converted into the (E)-2-butenedioate (1:2) salt in ethanol, yielding 4.4 parts (62.3%) of 2-amino-N-[2-[4-[[1-[(2-methyl-5-oxazolyl)methyl]-1H-benzimidazol-2-yl]amino]-1-piperidinyl]ethyl]benzamide (E)-2-butenedioate (1:2); mp. 219.6° C. (comp. 57).

EXAMPLE 26 a) To a stirred and cooled (−10° C.) mixture of 18 parts of carbondisulfide, 6.2 parts of N,N-methanetetraylbis[cyclohexanamine] and 134 parts of tetrahydrofuran there was added a solution of 10.5 parts of compound (30) in some tetrahydrofuran under a nitrogen atmosphere. The whole was allowed to reach room temperature and was stirred for 1 more hour. The reaction mixture was evaporated, yielding 12 parts (100%) of N-[1-(2-isothiocyanatoethyl)-4-piperidinyl]-1-[(2-methyl-5-oxazolyl)methyl]-1H-benzimidazol-2-amine (interm. 33).

b) A mixture of 3.3 parts of 3,4-pyridinediamine, 12 parts of intermediate (33) and 134 parts of tetrahydrofuran was refluxed for 18 hours. The reaction mixture was used as such for further synthesis. Theoretical yield: 15.2 parts (100%) of N-(4-amino-3-pyridinyl)-N'-[2-[4-[[1-[(2-methyl-5-oxazolyl)methyl]-1H-benzimidazol-2-yl]amino]-1-piperidinyl]ethyl]thiourea (interm. 34).

c) A mixture of 15 parts of intermediate (34), 10.7 parts of mercury(II)oxide, a few parts of sulfur and 134 parts of tetrahydrofuran was refluxed for 3 hours. The reaction mixture was filtered while hot over diatomaceous earth and the filtrate was evaporated. The residue was purified by column chromatography (silica gel; CH$_2$Cl$_2$/CH$_3$OH (NH$_3$) 90:10). The eluent of the desired fraction was evaporated and the residue was crystallized from 2,2'-oxybispropane. The product was filtered off and dried, yielding 0.54 parts (3.74%) of N-[2-[4-[[1-[(2-methyl-5-oxazolyl)methyl]-1H-benzimidazol-2-yl]amino]-1-piperidinyl]ethyl]-1H-imidazo[4,5-c]pyridin-2-amine hemihydrate; mp. 181.8° C. (comp. 83).

EXAMPLE 27

To a stirred and cooled (−70° C.) mixture of 16.5 parts of borontribromide in 66.5 parts of dichloromethane there was added dropwise a solution of 6.1 parts of compound (13) in 133 parts of dichloromethane. After stirring for 2 hours at room temperature, the reaction mixture was poured into NaHCO$_3$ (aq.). The whole was evaporated and the residue was taken up in a mixture of methanol and dichloromethane (10:90). The mixture was filtered over diatomaceous earth and the filtrate was evaporated. The residue was purified by twice by column chromatography (silica gel; CH$_2$Cl$_2$/CH$_3$OH(NH$_3$) 90:10) (silica gel; CH$_2$Cl$_2$/CH$_3$OH(NH$_3$) 95:5). The eluent of the desired fraction was evaporated and the residue was crystallized from acetonitrile. The product was filtered off and dried, yielding 4.2 parts (73.3%) of 4-[2-[4-[[1-[(2-methyl-5-oxazolyl)methyl]-1H-benzimidazol-2-yl]amino]-1-piperidinyl]ethyl]phenol hemihydrate; mp. 212.8° C. (comp. 47).

EXAMPLE 28

A mixture of 5.8 parts of compound (163) and 149 parts of hydrobromic acid (48%) was stirred for 1 hour at reflux temperature. After cooling, the reaction mixture was filtered and the filtrate was evaporated. The residue was co-evaporated with methylbenzene and then triturated in 2-propanone, yielding 4.8 parts (53.2%) of 4-[2-[4-[[1-[(2,5-dimethyl-4-oxazolyl)methyl]-1H-benzimidazol-2-yl]amino]-1-piperidinyl]e- thyl]phenol trihydrobromide sesquihydrate; mp. >280.0° C. (decomp.) (comp. 165).

EXAMPLE 29

A mixture of 5.3 parts of compound (70), 1 part of a solution of thiophene in methanol 4%, 2 parts of calcium oxide and 119 parts of methanol was hydrogenated for 18 hours at normal pressure and room temperature in the presence of 2 parts of palladium-on-charcoal catalyst 10%. After the calculated amount of hydrogen was taken up, the catalyst was filtered off and the filtrate was evaporated. The residue was purified by column chromatography (silica gel; $CH_2Cl_2/CH_3OH(NH_3)$ 95:5). The eluent of the desired fraction was evaporated and the residue was converted into the cyclohexylsulfamate (1:2) salt in 2-propanone. The salt was filtered off and dried, yielding 5.0 parts (63.3%) of 1-[(2-methyl-5-oxazolyl)methyl]-N-[1-[2-(2-pyridinylamino)ethyl]-4-piperidinyl]-1H-benzimidazol-2-amine cyclohexylsulfamate (1:2); mp. 212.3° C. (comp. 71).

EXAMPLE 30

To 5.4 parts of compound (89) there was added a solution of 0.52 parts of sodium hydroxide in 100 parts of water. After stirring for 3 hours at 40° C., there were added 1.27 parts of HCl (conc.). The whole was extracted with trichloromethane. The organic layer was discarted and the aqueous layer was evaporated. The residue was taken up in trichloromethane and this solution was dried, filtered and evaporated. The residue was converted into the cyclo-hexylsulfamate (1:2) salt in 2-propanol. The product was filtered off and dried, yielding 0.92 parts (9.5%) of 4-[[1-[(2-methyl-5-oxazolyl)methyl]-1H-benzimidazol-2-yl]amino]-1-piperidinepropanoic acid cyclohexylsulfamate (1:2); mp. 182.5° C. (comp. 91).

EXAMPLE 31

To a mixture of 2.5 parts of compound (9) and 70.5 parts of N,N-dimethyl-formamide under a nitrogen atmosphere there were added 0.384 parts of a dispersion of sodium hydride in mineral oil (50%) and, after stirring for ½ hour at room temperature and for ½ hour at 40° C., 1.14 parts of iodomethane. Stirring was continued for 18 hours at room temperature. There was added some ethanol and the whole was evaporated. The residue was partitioned between water and dichloromethane. The organic layer was separated, dried, filtered and evaporated. The residue was purified by column chromatography (silica gel; $CH_2Cl_2/CH_3OH(NH_3)$ 90:10). The eluent of the desired fraction was evaporated and the residue was converted into the ethanedioate (1:2) salt in 2-propanol. The product was filtered off and dried, yielding 0.92 parts (23.0%) of N-methyl-1-[(2-methyl-5-oxazolyl)methyl]-N-(1-methyl-4-piperidinyl)-1H-benzimidazol-2-amine ethanedioate (1:2); mp. 149.7° C. (comp. 54).

EXAMPLE 32 a) To a solution of 3.3 parts of compound (85) in 133 parts of dichloromethane there were added 2.18 parts of bis(1,1-dimethylethoxy)formic anhydride. After stirring for 2 hours at room temperature, the reaction mixture was diluted with water. The organic layer was separated, dried, filtered and evaporated. The residue was purified by column chromatography (silica gel; $CH_2Cl_2/CH_3OH$ 90:10). The eluent of the desired fraction was evaporated, yielding 3.4 parts (79.3%) of 1,1-dimethylethyl 4-[[1-[(2-methyl-5-oxazolyl)methyl]-1H-benzimidazol-2-yl]thio]-1-piperidinecarboxylate (comp. 86).

b) To a cooled (ice/salt bath) solution of 3.4 parts of compound (86) in 133 parts of dichloromethane there were added 1.38 parts of 3-chlorobenzenecarboperoxoic acid. The whole was stirred for 1½ hour while cooling and was then allowed to reach room temperature. The reaction mixture was washed with $NaHCO_3$ (aq.) and water and was then dried, filtered and evaporated, yielding 4.1 parts (100%) of 1,1-dimethylethyl 4-[[1-[(2-methyl-5-oxazolyl)methyl]-1H-benzimidazol-2-yl]sulfinyl]-1-piperidinecarboxylate (comp. 87).

EXAMPLE 33 a) A mixture of 14.2 parts of compound (3), 2 parts of a solution of thiophene in methanol 4%, 5 parts of polyoxymethylene and 198 parts of methanol was hydrogenated at normal pressure and 50° C. in the presence of 2 parts of palladium-on-charcoal catalyst 10%. After the calculated amount of hydrogen was taken up, the catalyst was filtered off and the filtrate was evaporated. The residue was partitioned between dichloromethane and $NH_4OH$ (dil.). The organic layer was separated, dried, filtered and evaporated. The residue was purified by column chromatography (silica gel; $CH_2Cl_2/CH_3OH(NH_3)$ 95:5). The eluent of the desired fraction was evaporated and the residue was converted into the trihydrochloride salt in a mixture of 2-propanone and ethanol by addition of 2-propanol saturated with HCl. The salt was filtered off and dried, yielding 12.3 parts (56.8%) of 1-[(2-methyl-5-oxazolyl)methyl]-N-(1-methyl-4-piperidinyl)-1H-benzimidazol-2-amine trihydrochloride dihydrate; mp. 177.1° C. (comp. 24).

b) 3 Parts of compound (9) and 3 parts of [R-(R*,R*)]-2,3-dihydroxy-1,4-butanedioic acid were separately boiled in 119 parts and 23.7 parts of acetonitrile, respectively. The two mixtures were combined and the whole was left to crystallize. The product was filtered off and dried, yielding 4.53 parts (77.5%) of (+)-1-[(2-methyl-5-oxazolyl)methyl]-N-(1-methyl-4-piperidinyl)-1H-benzimidazol-2-amine [R-(R*,R*)]-2,3-dihydroxybutanedioate (1:2) hemihydrate; mp. 155.9° C.; $[\alpha]_D^{20} = +14.76°$ (conc.=1% in methanol) (comp. 26).

c) To a stirred and refluxing mixture of 3 parts of compound (9), 39.5 parts of ethanol and 79 parts of 2-propanone there were added portionwise 4.5 parts of cyclohexyl sulfamic acid. Stirring was continued and the whole was left to crystallize upon cooling. The product was filtered off and recrystallized from 2-propanol, yielding 3.1 parts (49.7%) of 1-[(2-methyl-5-oxazolyl)methyl]-N-(1-methyl-4-piperidinyl)-1H-benzimidazol-2-amine cyclohexylsulfamate (1:2) hemihydrate; mp. 199.5° C. (comp. 33).

d) To a heated (40° C.) solution of 5.04 parts of 2-hydroxy-1,2,3-propanetricarboxylic acid in 39 parts of 2-propanol there was added a solution of 2.6 parts of compound (9) in 156 parts of 2-propanol. The precipitate was filtered off, dried in vacuo at room temperature and stirred in 156 parts of 2-propanol. Subsequently, the solid was taken up in 156 parts of 2-propanol and a solution of 1 part of 2-hydroxy-1,2,3-propanetricarboxylic acid in 2-propanol was added. The salt was filtered off and stirred in 156 parts of 2-propanol, yielding 2.95 parts (49.2%) of 1-[(2-methyl-5-oxazolyl)methyl]-N-(1-methyl-4-piperidinyl)-1H-benzimidazol-2-amine hemihydrate 2-propanolate (2:1) 2-hydroxy- 1,2,3-propanetricarboxylate (1:2); mp. 85.2° C. (comp. 51).

e) 0.294 Parts of compound (9) were crystallized from a mixture of acetonitrile and water (9:1). The product was filtered off and dried, yielding 0.193 parts (56.2%) of 1-[(2-methyl-5-oxazolyl)methyl]-N-(1-methyl-4-piperidinyl)-1H-benzimidazol-2-amine trihydrate; mp. 94.5° C. (comp. 84).

EXAMPLE 34

To a solution of 13 parts of compound (1) in 266 parts of dichloromethane there were added dropwise 5.45 parts of ethyl chloroformate and 5.7 parts of N,N-diethylethanamine. The whole was stirred and refluxed for 17 hours. The reaction mixture was washed with water, dried, filtered and evaporated. The residue was purified by column chromatography (silica gel; CH$_2$Cl$_2$/CH$_3$OH 90:10). The eluent of the desired fraction was evaporated, yielding 11 parts (89.9%) of ethyl 4-[[1-[(2-methyl-5-oxazolyl)methyl]-1H-benzimidazol-2-yl]methyl]-1-piperidinecarboxylate (comp. 4).

EXAMPLE 35

A mixture of 17 parts of methyl (cis+trans)-4-amino-3-methyl-1-piperidinecarboxylate, 25 parts of intermediate 24 and 7 parts of copper was stirred for 6 hours at 150° C. After cooling, the reaction mixture was taken up in dichloromethane and the whole was filtered over diatomaceous earth. The filtrate was washed with NaOH (dil.) and water, dried, filtered and evaporated. The residue was purified by column chromatography (silica gel; CH$_2$Cl$_2$/CH$_3$OH(NH$_3$) 98:2). The eluent of the desired fraction was evaporated, yielding 15.6 parts (40.7%) of (±)-methyl (cis+trans)-3-methyl-4-[[1-[(2-methyl-5-oxazolyl)methyl]-1H-benzimidazol-2-yl]amino]-1-piperidinecarboxylate (comp. 143).

All compounds listed in Tables 1-6 were prepared following methods of preparation described in examples 13-35, as is indicated in the column Ex. No.

TABLE 1

| Co. No. | Ex. No. | B | L | Physical data |
|---|---|---|---|---|
| 1 | 10 | CH$_2$ | C$_6$H$_5$—CH$_2$— | mp. 108.6° C. |
| 2 | 9 | NH | C$_2$H$_5$OCO— | — |
| 3 | 16 | NH | H | mp. 227.2° C. |
| 4 | 34 | CH$_2$ | C$_2$H$_5$OCO— | — |
| 5 | 16 | CH$_2$ | H | mp. 230° C./3/2* |
| 6 | 18 | CH$_2$ | [S,N-heterocycle with CH$_3$, (CH$_2$)$_2$—] | mp. 172.9° C. |
| 7 | 18 | NH | [S,N-heterocycle with CH$_3$, (CH$_2$)$_2$—] | mp. 193.5° C./½H$_2$O |
| 8 | 18 | NH | [pyridine-N fused with CH$_3$, (CH$_2$)$_2$—] | mp. 203.2° C. |
| 9 | 17 | NH | CH$_3$ | mp. 78.2° C./½H$_2$O |
| 10 | 18 | NH | [S,N-heterocycle with CH$_3$, (CH$_2$)$_2$—] | mp. 199.6° C./½H$_2$O |

TABLE 1-continued

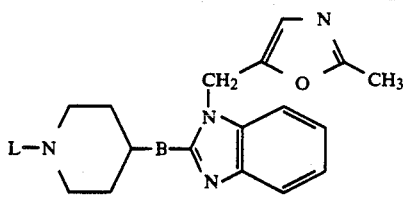

| Co. No. | Ex. No. | B | L | Physical data |
|---|---|---|---|---|
| 11 | 18 | NH | [thiazine-methyl-propyl group] | mp. 133.0° C./C₂H₅OH/* |
| 12 | 18 | CH₂ | [thiazine-methyl-propyl group] | mp. 176.1° C. |
| 13 | 18 | NH | 4-CH₃O—C₆H₄—(CH₂)₂— | mp. 134.3° C./½H₂O |
| 14 | 18 | CH₂ | [thiazine-methyl-propyl group] | mp. 173.8° C. |
| 15 | 17 | CH₂ | CH₃ | mp. 196.1° C./2* |
| 16 | 18 | CH₂ | [pyrido-pyrimidinone group] | mp. 182.1° C. |
| 17 | 18 | CH₂ | 4-CH₃O—C₆H₄—(CH₂)₂— | mp. 144.2° C./3/2* |
| 18 | 19a | CH₂ | NC—CH₂— | mp. 189.6° C./3/2* |
| 19 | 19b | CH₂ | H₂N—(CH₂)₂— | — |
| 20 | 19c | CH₂ | [pyrimidinyl-NH-(CH₂)₂-] | mp. 173.7° C./2(COOH)₂ |
| 21 | 20 | NH | [pyridyl-(CH₂)₂-] | mp. 184.6° C./* |
| 22 | 18 | NH | [oxazolidinone-N-(CH₂)₂-] | mp. 196.9° C./3/2* H₂O |
| 23 | 19a | NH | NC—CH₂— | mp. 191.0° C. |
| 24 | 33a | NH | CH₃ | mp. 177.1° C./3HCl 2H₂O |
| 25 | 18 | NH | H₅C₂-N—[triazolinone]—N—(CH₂)₂— | mp. 131.8° C./½H₂O 2* |
| 26 | 33b | NH | CH₃ | mp. 155.9° C./½H₂O 2** [α]$_D^{20}$ 1% CH₃OH = +14.76° |

TABLE 1-continued

[Structure: L—N(piperidine)—B—benzimidazole with N-CH2-oxazole-CH3 substituent]

| Co. No. | Ex. No. | B | L | Physical data |
|---|---|---|---|---|
| 27 | 18 | NH | [2,3-dihydro-1H-quinazoline-2,4-dione-3-yl-(CH2)2—] | mp. 142.7° C. |
| 28 | 18 | NH | $C_6H_5$—CH=CH—CH2— | mp. 155.0° C./(E)/H2O |
| 29 | 18 | NH | [2-methyl-oxazol-4-yl-CH2—] | mp. 203.7° C./2* |
| 30 | 19b | NH | $H_2N$—(CH2)2— | — |
| 31 | 22 | NH | $CH_3$—NH—CO—NH—(CH2)2— | mp. 203.4° C. |
| 32 | 18 | NH | $(CH_3)_2CH$—NH—CO—(CH2)2— | mp. 78.5° C./½H2O |
| 33 | 33c | NH | CH3 | mp. 199.5° C./2*** ½H2O |
| 34 | 18 | NH | [thiophen-2-yl-(CH2)2—] | mp. 188.8° C./H2O 3/2* |
| 35 | 21a | NH | $C_6H_5O$—CH2—CH(OH)—CH2— | mp. 173.0° C. |
| 36 | 21a | NH | HO—(CH2)2— | mp. 201.2° C./2* $CH_3CH(OH)CH_3$ |
| 37 | 19c | NH | [pyrimidin-2-yl—O—(CH2)2—] | mp. 167.4° C./2* |
| 38 | 18 | NH | $CH_3$—CH2—O—(CH2)2— | mp. 186.0° C./2(COOH)2 |
| 39 | 18 | NH | [1,2,4-triazine-methyl-pyrimidinone-(CH2)2—] | mp. 206.3° C./5/2* |
| 40 | 17 | NH | [3,4,5-trimethoxybenzyl-CH2—] | mp. 112.8° C./H2O |
| 41 | 17 | NH | $c.C_6H_{11}$— | mp. 108.2° C./H2O |
| 42 | 23 | NH | [3-amino-pyrazine-2-carboxamido-(CH2)2—] | mp. 134.2° C./H2O |
| 43 | 19c | NH | [pyrimidin-2-yl-NH—(CH2)2—] | mp. 184.1° C. |

TABLE 1-continued

| Co. No. | Ex. No. | B | L | Physical data |
|---|---|---|---|---|
| 44 | 18 | NH | (chromen-2-one)-3-(CH$_2$)$_2$— | mp. 212.8° C./½H$_2$O 2* |
| 45 | 23 | NH | (1-methylpyrrol-2-yl)-C(O)-NH-(CH$_2$)$_2$— | mp. 209.3° C./2(COOH)$_2$ |
| 46 | 17 | NH | CH$_3$—CH$_2$— | mp. 105.9° C./½H$_2$O |
| 47 | 27 | NH | 4-HO—C$_6$H$_4$—(CH$_2$)$_2$— | mp. 212.8° C./½H$_2$O |
| 48 | 18 | NH | CH$_3$—CO—(CH$_2$)$_3$— | mp. 91.5° C./½H$_2$O |
| 49 | 22 | NH | CH$_3$—NH—CS—NH—(CH$_2$)$_2$— | mp. 180.8° C./H$_2$O 2*** |
| 50 | 18 | NH | (triazinone derivative)-(CH$_2$)$_2$— | mp. 188.3° C. |
| 51 | 33d | NH | CH$_3$ | mp. 85.2° C./½H$_2$O 2****  ¼CH$_3$CH(OH)CH$_3$ |
| 52 | 18 | NH | (benzimidazol-2(3H)-one)-N-(CH$_2$)$_3$— | mp. 204.4° C. |
| 53 | 18 | NH | (pyrimidinone derivative)-(CH$_2$)$_2$— | mp. 169.5° C./H$_2$O |
| 54 | 31 | N(CH$_3$) | CH$_3$ | mp. 149.7° C./2(COOH)$_2$ |
| 55 | 18 | NH | (pyrido-pyrimidinone)-(CH$_2$)$_2$— | mp. 177.1° C./ |
| 56 | 18 | NH | 4-F—C$_6$H$_4$—O—(CH$_2$)$_3$— | mp. 91.3° C./H$_2$O |
| 57 | 25 | NH | 2-NH$_2$-C$_6$H$_4$-C(O)-NH-(CH$_2$)$_2$— | mp. 219.6° C./2* |

TABLE 1-continued

| Co. No. | Ex. No. | B | L | Physical data |
|---|---|---|---|---|
| 58 | 18 | NH | (isoxazole-methyl-pyrimidinone-(CH$_2$)$_2$—) | mp. 180.1° C. |
| 59 | 18 | NH | (methyl-pyridazinone-N-(CH$_2$)$_2$—) | mp. 130.8° C. |
| 60 | 23 | NH | (nicotinoyl-O-(CH$_2$)$_2$—) | mp. 186.5° C./2(COOH)$_2$ |
| 61 | 18 | NH | (H$_2$N-guanidinyl-methyl-CH$_3$-C(=O)-(CH$_2$)$_2$—) | mp. 205.4° C./H$_2$O |
| 62 | 18 | NH | (CH$_3$-NH-guanidinyl-methyl-CH$_3$-C(=O)-(CH$_2$)$_2$—) | mp. 208.8° C./2* |
| 63 | 13 | O | CH$_3$—CH$_2$—O—CO— | — |
| 64 | 16 | O | H | mp. 160.9° C./3/2(COOH)$_2$ |
| 65 | 24 | NH | (1-methyl-indole-2-C(=O)-NH-(CH$_2$)$_2$—) | mp. 104.0° C. |
| 66 | 17 | O | CH$_3$ | mp. 166.3° C./2* |
| 67 | 14b | NH | H | mp. 279.6° C./3HBr |
| 68 | 21c | NH | (1-methyl-imidazole-2-S-(CH$_2$)$_2$—) | mp. 195.2° C./½H$_2$O 3(COOH)$_2$ |
| 69 | 20 | NH | CH$_3$—CO—(CH$_2$)$_2$— | mp. 173.1° C./3HBr 5/2H$_2$O |
| 70 | 18 | NH | (5-bromo-pyridin-2-yl-NH-(CH$_2$)$_2$—) | — |

TABLE 1-continued

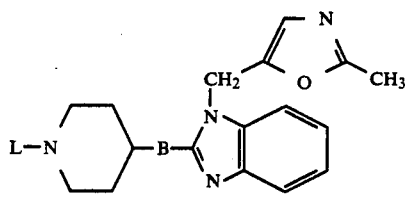

| Co. No. | Ex. No. | B | L | Physical data |
|---|---|---|---|---|
| 71 | 29 | NH | 2-pyridyl-NH—(CH₂)₂— | mp. 212.3° C./2*** |
| 72 | 18 | NH | 4-(tert-butyl)phenyl-C(O)—(CH₂)₃— | mp. 107.1° C./H₂O |
| 73 | 18 | NH | (imidazo-fused pyrimidinyl)—NH—(CH₂)₂— | mp. 230.0° C./H₂O 5/2* |
| 74 | 19c | NH | H₂N—(thiadiazol-yl)—NH—(CH₂)₂— | mp. 142.0° C./½H₂O |
| 75 | 19c | NH | thiazol-2-yl—NH—(CH₂)₂— | mp. 195.0° C./2*** |
| 76 | 19c | NH | 5-methyl-1,3,4-thiadiazol-2-yl—NH—(CH₂)₂— | mp. 90.3° C./½H₂O |
| 77 | 23 | NH | furan-3-yl—C(O)—NH—(CH₂)₂— | mp. 181.2° C. |
| 78 | 18 | NH | (CH₃)₂CH— | mp. 82.5° C./½H₂O |
| 79 | 19c | NH | (4-oxo-1H-pyrimidin-2-yl)—NH—(CH₂)₂— | mp. 177.5° C./3/2* H₂O |
| 80 | 19c | NH | 6-chloropyridazin-3-yl—NH—(CH₂)₂— | — |
| 81 | 29 | NH | pyridazin-3-yl—NH—(CH₂)₂— | mp. 84.5° C. |

TABLE 1-continued

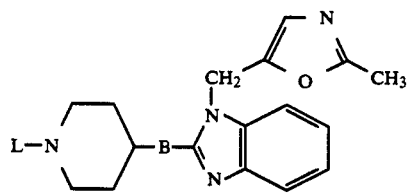

| Co. No. | Ex. No. | B | L | Physical data |
|---|---|---|---|---|
| 82 | 18 | NH | (structure: N-(CH₂)₂- attached to uracil-like ring) | mp. 199.7° C./3/2* |
| 83 | 26 | NH | (structure: pyridine-NH-C(=N)-NH-(CH₂)₂-) | mp. 181.8° C./½H₂O |
| 84 | 33e | NH | CH₃ | mp. 94.5° C./3H₂O |
| 85 | 14 | S | H | 2*** |
| 86 | 32a | S | (CH₃)₃CH—O—CO— | — |
| 87 | 32b | S(O) | (CH₃)₃CH—O—CO— | — |
| 88 | 15b | S(O) | H | mp. 172.4° C./3.2* |
| 89 | 18 | NH | CH₃—CH₂—O—CO—(CH₂)₂— | mp. 173.6° C./2* |
| 90 | 10 | NH | CH₃ | mp. 133.1° C. |
| 91 | 30 | NH | HOCO—(CH₂)₂— | mp. 182.5° C./2*** |
| 92 | 17 | S | CH₃ | mp. 184.2° C./2* |
| 93 | 17 | S | CH₃ | mp. 88.7° C./ |

*(E)-2-butenedioate
**(+)-[R-(R*,R*)]-2,3-dihydroxybutanedioate
***cyclohexylsulfamate
****2-hydroxy-1,2,3-propanetricarboxylate

TABLE 2

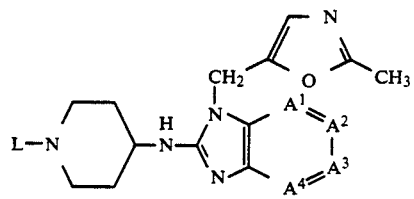

| Co. No. | Ex. No. | —A¹=A²—A³=A⁴— | L | Physical data |
|---|---|---|---|---|
| 94 | 11 | —N=CH—CH=CH— | CH₃—CH₂—O—CO— | — |
| 95 | 16 | —N=CH—CH=CH— | H | mp. 122.5° C/½H₂O |
| 96 | 17 | —N=CH—CH=CH— | CH₃ | mp. 141.6° C. |
| 97 | 18 | —N=CH—CH=CH— | 4-F—C₆H₄—O—(CH₂)₃— | mp. 104.0° C./H₂O |
| 98 | 18 | —N=CH—CH=CH— | CH₂=CH—CH₂— | mp. 92.4° C./½H₂O |
| 99 | 18 | —N=CH—CH=CH— | 4-CH₃O—C₆H₄—(CH₂)₂— | mp. 134.2° C. |
| 100 | 18 | —N=CH—CH=CH— | (theophylline-(CH₂)₂—) | mp. 177.1° C. |
| 101 | 20 | —N=CH—CH=CH— | (pyridin-2-yl)-(CH₂)₂— | mp. 110.3° C./3/2H₂O |
| 102 | 11 | —CH=CH—N=CH— | CH₃—CH₂—O—CO— | mp. 123.8° C./3H₂O |
| 103 | 14b | —CH=CH—N=CH— | H | mp. 204.6° C. |

TABLE 2-continued

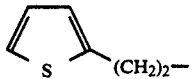

| Co. No. | Ex. No. | —A$^1$=A$^2$—A$^3$=A$^4$— | L | Physical data |
|---|---|---|---|---|
| 104 | 11 | —N=CH—N=CH— | CH$_3$—CH$_2$—O—CO— | mp. 187.7° C. |
| 105 | 17 | —CH=CH—N=CH— | CH$_3$ | mp. 174.6° C./H$_2$O |
| 106 | 18 | —CH=CH—N=CH— | 4-CH$_3$O—C$_6$H$_4$—(CH$_2$)$_2$— | mp. 191.5° C. |
| 107 | 18 | —N=CH—CH=CH— | 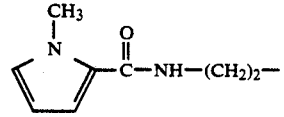 | mp. 88.9° C. |
| 108 | 19a | —N=CH—CH=CH— | NC—CH$_2$— | — |
| 109 | 19b | —N=CH—CH=CH— | H$_2$N—(CH$_2$)$_2$— | — |
| 110 | 23 | —N=CH—CH=CH— | 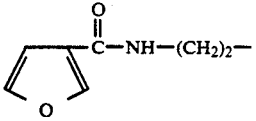 | mp. 84.5° C./½H$_2$O |
| 111 | 11 | —CH=N—CH=CH— | CH$_3$—CH$_2$—O—CO— | 166.7° C./H$_2$O |
| 112 | 23 | —N=CH—CH=CH— | 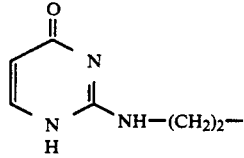 | mp. 173.1° C. |
| 113 | 19c | —N=CH—CH=CH— | 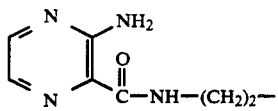 | mp. 180.0° C./5/2* |
| 114 | 14b | —N=CH—N=CH— | H | — |
| 115 | 17 | —N=CH—N=CH— | CH$_3$ | mp. 148.1° C. |
| 116 | 18 | —N=CH—N=CH— | 4-CH$_3$O—C$_6$H$_4$—(CH$_2$)$_2$— | mp. 199.8° C. |
| 117 | 23 | —N=CH—CH=CH— | 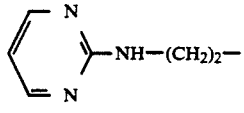 | mp. 103.5° C. |
| 118 | 19c | —N=CH—CH=CH— | 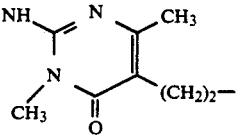 | mp. 189.2° C. |
| 119 | 14b | —CH=N—CH=CH— | H | — |
| 120 | 17 | —CH=N—CH=CH— | CH$_3$ | mp. 202.2° C./ ½CH$_3$CH(OH)CH$_3$ 3/2* |
| 121 | 21a | —N=CH—CH=CH— | C$_6$H$_5$O—CH$_2$—CH(OH)—CH$_2$— | mp. 146.9° C. |
| 122 | 18 | —N=CH—CH=CH— | (structure with CH$_3$—NH, pyrimidine ring, (CH$_2$)$_2$—) | mp. 201.4° C./5/2* |

TABLE 2-continued

| Co. No. | Ex. No. | —A¹=A²—A³=A⁴— | L | Physical data |
|---|---|---|---|---|
| 123 | 18 | —N=CH—CH=CH— | (complex structure with two N-CH₃ triazine/pyrimidinone linked via (CH₂)₂—) | mp. 91.8° C./3/2H₂O |
| 124 | 28 | —N=CH—CH=CH— | 4-HO—C₆H₄—(CH₂)₂— | mp. 179.2° C./½H₂O |
| 125 | 18 | —N=CH—CH=CH— | (tetrahydropyridine-CH₃-pyrimidinone with (CH₂)₂—) | mp. 123.3° C./2H₂O |
| 126 | 18 | —N=CH—CH=CH— | (6-chloropyridazin-3-yl)—N—(CH₂)₂— | mp. 214.6° C. |
| 127 | 18 | —CH=N—CH=CH— | 4-CH₃O—C₆H₄—(CH₂)₂— | mp. 201.9° C./3/2* |
| 128 | 25 | —N=CH—CH=CH— | 2-NH₂—C₆H₄—C(O)—NH—(CH₂)₂— | mp. 193.2° C. |

*(E)-2-butenedioate

TABLE 3

| Co. No. | Ex. No. | R | n | Rar | R¹ | L | Physical data |
|---|---|---|---|---|---|---|---|
| 129 | 15a | H | 1 | H | CH₂OH | CH₃CH₂O—CO— | mp. 178.4° C. |
| 130 | 10 | H | 0 | H | CH₃ | CH₃CH₂O—CO— | mp. 133.4° C. |
| 131 | 16 | H | 0 | H | CH₃ | H | mp. 188.1° C./2(COOH)₂ |
| 132 | 17 | H | 0 | H | CH₃ | CH₃ | mp. 217.4° C./½C₂H₅OH 2(COOH)₂ |
| 133 | 10 | H | 2 | H | CH₃ | CH₃CH₂O—CO— | mp. 125.4° C./HCl ½H₂O |
| 134 | 16 | H | 2 | H | CH₃ | H | 2(COOH)₂ |
| 135 | 17 | H | 2 | H | CH₃ | CH₃ | mp. 197.7° C./2(COOH)₂ |
| 136 | 11 | H | 1 | 6-CH₃O— | CH₃ | CH₃ | mp. 152.4° C. |
| 137 | 11 | H | 1 | 5-CH₃O— | CH₃ | CH₃CH₂O—CO— | |
| 138 | 16 | H | 1 | 5-CH₃O— | CH₃ | H | mp. 199.2° C./½H₂O 2* |

TABLE 3-continued

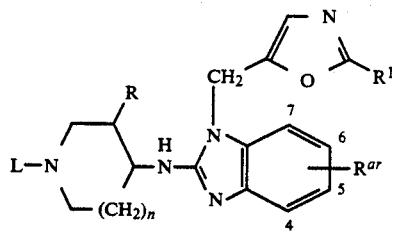

| Co. No. | Ex. No. | R | n | R$^{ar}$ | R$^1$ | L | Physical data |
|---|---|---|---|---|---|---|---|
| 139 | 17 | H | 1 | 5-CH$_3$O— | CH$_3$ | CH$_3$ | mp. 187.4° C./2** |
| 140 | 28 | H | 1 | 5-HO— | CH$_3$ | CH$_3$ | mp. 131.9° C./H$_2$O |
| 141 | 15a | H | 1 | H | CH$_2$OH | (CH$_3$)$_3$CO—CO— | mp. 132.3° C. |
| 142 | 11 | H | 1 | 6-F | CH$_3$ | CH$_3$ | mp. 204.6° C./5/2* |
| 143 | 35 | CH$_3$ | 1 | H | CH$_3$ | CH$_3$O—CO— | (cis + trans) |
| 144 | 14b | CH$_3$ | 1 | H | CH$_3$ | H | (cis + trans) |
| 145 | 17 | CH$_3$ | 1 | H | CH$_3$ | CH$_3$ | mp. 163.0° C./ (cis + trans)/2** |
| 146 | 15b | H | 1 | H | CH$_2$OH | H | mp. 279.5° C./ 3HCl ½H$_2$O |
| 147 | 15c | H | 1 | H | CH$_2$OH | 4-CH$_3$O—C$_6$H$_4$—(CH$_2$)$_2$— | mp. 130.7° C./H$_2$O |
| 148 | 17 | H | 1 | H | CH$_2$OH | CH$_3$ | mp. 118.5° C./H$_2$O |

*(E)-2-butenedioate
**cyclohexylsulfamate

TABLE 4

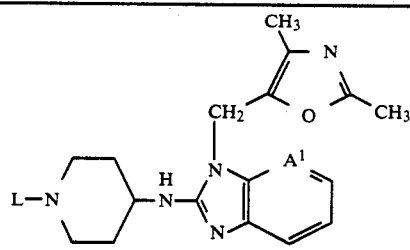

| Co. No. | Ex. No. | A$^1$ | L | Physical data |
|---|---|---|---|---|
| 149 | 10 | CH | CH$_3$CH$_2$O—CO— | mp. 147.8° C. |
| 150 | 14b | CH | H | mp. 174.9° C./½H$_2$O |
| 151 | 17 | CH | CH$_3$ | mp. 125.9° C. |
| 152 | 18 | CH | 4-CH$_3$O—C$_6$H$_4$—(CH$_2$)$_2$— | mp. 138.8° C./½H$_2$O |
| 153 | 12 | N | CH$_3$CH$_2$O—CO— | mp. 132.6° C. |
| 154 | 14b | N | H | mp. 162.9° C. |

TABLE 4-continued

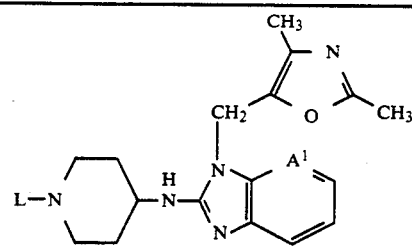

| Co. No. | Ex. No. | A$^1$ | L | Physical data |
|---|---|---|---|---|
| 155 | 17 | N | CH$_3$ | mp. 114.8° C./H$_2$O |
| 156 | 18 | N | 4-CH$_3$O—C$_6$H$_4$—(CH$_2$)$_2$— | mp. 112.7° C./H$_2$O |
| 157 | 28 | N | 4-HO—C$_6$H$_4$—(CH$_2$)$_2$— | mp. 143.2° C./H$_2$O |

TABLE 5

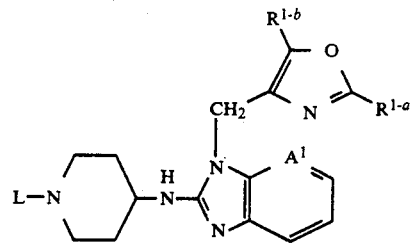

| Co. No. | Ex. No. | A$^1$ | R$^{1-a}$ | R$^{1-b}$ | L | Physical data |
|---|---|---|---|---|---|---|
| 158 | 11 | N | CH$_3$ | CH$_3$ | CH$_3$ | mp. 173.2° C./2* |
| 159 | 10 | CH | CH$_3$ | CH$_3$ | (CH$_3$)$_3$CO—CO— | — |
| 160 | 15b | CH | CH$_3$ | CH$_3$ | H | mp. 208.5° C./2* |
| 161 | 10 | CH | CH$_3$ | H | CH$_3$ | mp. 183.4° C./½H$_2$O/3/2* |
| 162 | 10 | CH | H | CH$_3$ | CH$_3$ | CH$_3$CH(OH)CH$_3$/3/2* |
| 163 | 18 | CH | CH$_3$ | CH$_3$ | 4-CH$_3$O—C$_6$H$_4$—(CH$_2$)$_2$— | mp. 173.4° C./½H$_2$O 2* |
| 164 | 17 | CH | CH$_3$ | CH$_3$ | CH$_3$ | mp. 183.9° C./C$_2$H$_5$OH 3/2* |
| 165 | 28 | CH | CH$_3$ | CH$_3$ | 4-HO—C$_6$H$_4$—(CH$_2$)$_2$— | mp. >280° C./3HBr 3/2H$_2$O |
| 166 | 10 | CH | H | H | CH$_3$—CH$_2$—O—CO— | |
| 167 | 16 | CH | H | H | H— | |

TABLE 5-continued

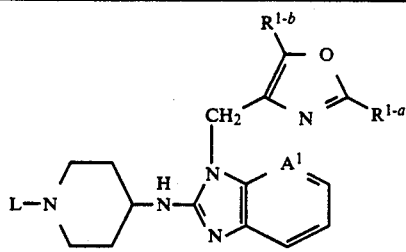

| Co. No. | Ex. No. | $A^1$ | $R^{1-a}$ | $R^{1-b}$ | L | Physical data |
|---|---|---|---|---|---|---|
| 168 | 17 | CH | H | H | $CH_3$ | |

*(E)-2-butenedioate

C. PHARMACOLOGICAL EXAMPLE

EXAMPLE 9

The useful anti-allergic and anti-histaminic properties of the compounds of formula (I) can be demonstrated, e.g., in the test "Protection of rats from compound 48/80-induced lethality" which is described in U.S. Pat. No. 4,556,660, incorporated herein by reference. The compounds of formula (I) were administered subcutaneously and/or orally to rats. The $ED_{50}$-value (in mg/kg) for the compounds 3; 9; 12; 14; 15; 16 or 17 was found to range from 0.01 mg/kg to 0.04 mg/kg.

We claim:

1. A compound having the formula:

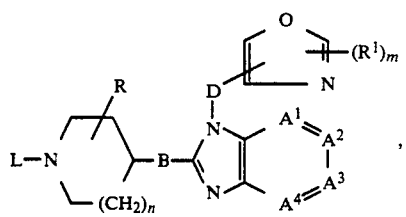

a pharmaceutically acceptable addition salt or a stereochemically isomeric form thereof, wherein:

—$A^1$=$A^2$—$A^3$=$A^4$— represents a bivalent radical having the formula

| —N=CH—CH=CH— | (a-2), |
| —CH=N—CH=CH— | (a-3), |
| —CH=CH—N=CH— | (a-4), |
| —CH=CH—CH=N— | (a-5), |
| —N=CH—N=CH— | (a-6), | or

| —CH=N—CH=N— | (a-7), | wherein one or two hydrogen atoms in said radicals (a-2) to (a-7) may each independently be replaced by halo, $C_{1-6}$alkyl, $C_{1-6}$alkyloxy, hydroxy or trifluoromethyl;

R represents hydrogen or $C_{1-4}$alkyl;
$R^1$ represents hydrogen, $C_{1-6}$alkyl or hydroxy$C_{1-6}$alkyl;
m is 1 or 2;
D represents $C_{1-4}$alkanediyl;
B represents $NR^2$, $CH_2$, O, S, SO or $SO_2$ wherein $R^2$ is hydrogen or $C_{1-4}$alkyl;
n is 0, 1 or 2; and
L represents hydrogen; $C_{1-12}$alkyl; $C_{3-6}$cycloalkyl; $C_{3-6}$alkenyl optionally substituted with aryl; $C_{1-6}$alkylcarbonyl; $C_{1-6}$alkyloxy-carbonyl; arylcarbonyl; aryl$C_{1-6}$alkyloxycarbonyl; or a radical of the formula:

| —Alk—$R^3$ | (b-1); |
| —Alk—Y—$R^4$ | (b-2); |
| —Alk—$Z^1$—C(=X)—$Z^2$—$R^5$ | (b-3); | or

| —$CH_2$—CHOH—$CH_2$—O—$R^6$ | (b-4); | wherein $R^3$ represents cyano, aryl or Het;
$R^4$ represents hydrogen, aryl, Het or $C_{1-6}$alkyl optionally substituted with aryl or Het;
$R^5$ represents hydrogen, aryl, Het or $C_{1-6}$alkyl optionally substituted with aryl or Het;
$R^6$ represents aryl or naphthalenyl;
Y represents O, S, $NR^7$ said $R^7$ being hydrogen, $C_{1-6}$alkyl or $C_{1-6}$alkylcarbonyl;
$Z^1$ and $Z^2$ each independently represent O, S, $NR^8$ or a direct bond, said $R^8$ being hydrogen or $C_{1-6}$alkyl; and
X represent O, S or $NR^9$; said $R^9$ being hydrogen, $C_{1-6}$alkyl or cyano; each Alk independently is $C_{1-6}$alkanediyl;

wherein each Het represents:
(i) an optionally substituted five- or six-membered heterocyclic ring containing 1, 2, 3 or 4 heteroatoms selected from oxygen, sulfur and nitrogen, provided that no more than 2 oxygen and/or sulfur atoms are present;
(ii) an optionally substituted five- or six-membered heterocyclic ring containing 1 or 2 heteroatoms selected from oxygen, sulfur and nitrogen, being fused with an optionally substituted five- or six-membered ring through 2 carbon atoms or 1 carbon and 1 nitrogen atom, containing in the remainder of the fused ring only carbon atoms; or
(iii) an optionally substituted five- or six-membered heterocyclic ring containing 1 or 2 heteroatoms selected from oxygen, sulfur and nitrogen, being fused with an optionally substituted five- or six-membered heterocyclic ring through 2 carbon atoms or 1 carbon and 1 nitrogen atom, containing in the remainder of the fused ring 1 or 2 heteroatoms selected from oxygen, sulfur and nitrogen;

wherein when Het is a monocyclic ring system Het may optionally be substituted with up to 4 substituents; and when Het is a bicyclic ring system Het may optionally be substituted with up to 6 substituents, said substituents being selected from halo, amino, mono- and di($C_{1-6}$alkyl)amino, aryl$C_{1-6}$alkylamino, nitro, cyano, aminocarbonyl, $C_{1-6}$alkyl, $C_{1-6}$alkyloxy, $C_{1-6}$alkylthio, $C_{1-6}$alkyloxy-carbonyl, $C_{1-6}$alkyloxy$C_{1-6}$alkyl, $C_{1-6}$alkyloxycarbonyl$C_{1-6}$alkyl, hydroxy, mercapto, hydroxy$C_{1-6}$alkyl, $C_{1-6}$alkylcarbonyloxy, aryl, aryl$C_{1-6}$alkyl, carboxyl, $C_{1-6}$alkylaminocarbonylamino, arylaminocarbonylamino, oxo or thio;

wherein in the foregoing, each aryl is phenyl optionally substituted with 1, 2 or 3 substituents each independently selected from halo, hydroxy, nitro, cyano, trifluoromethyl, $C_{1-6}$alkyl, $C_{1-6}$alkyloxy, $C_{1-6}$alkylthio, mercapto, amino, mono- and di-($C_{1-6}$alkyl)-amino, carboxyl, $C_{1-6}$alkyloxycarbonyl and $C_{1-6}$alkylcarbonyl.

2. A compound according to claim 1 wherein R represents hydrogen; m is 1; and $R^1$ represents hydrogen or $C_{1-6}$alkyl.

3. A compound according to claim 1 wherein —$A^1$=$A^2$—$A^3$=$A^4$— represents a bivalent radical having the formula —N=CH—CH=CH— (a-2) wherein one hydrogen atom in said radical (a-2) may be replaced by halo, $C_{1-6}$alkyloxy or hydroxy;

R represents hydrogen or methyl;
$R^1$ represents hydrogen, methyl or hydroxymethyl;
m is 1 or 2;
D represents $CH_2$;
B represents NH, $NCH_3$, $CH_2$, O, S or SO;
n is 0, 1 or 2; and
L represents hydrogen, $C_{1-4}$alkyl, cyclohexyl, propenyl, 3-phenylpropenyl, $C_{1-4}$alkyloxycarbonyl, or L represents a radical of the formula:

—Alk—$R^3$ (b-1);

—Alk—Y—$R^4$ (b-2);

—Alk—$Z^1$—C(=X)—$Z^2$—$R^5$ (b-3);

or

—$CH_2$—CHOH—$CH_2$—O—$R^6$ (b-4);

wherein:
each Alk independently represents $C_{1-4}$alkanediyl;
$R^3$ represents phenyl, hydroxyphenyl, $C_{1-4}$alkyloxyphenyl, 3,4,5-trimethoxyphenyl, pyridinyl, thienyl, 2-methyl-5-oxazolyl, 4,5-dihydro-4-ethyl-5-oxo-1H-tetrazolyl, 2,3-dihydro-6-methyl-3-oxopyridazinyl, 2-oxo-3-oxazolidinyl, 2-(amino or methylamino)-3,4-dihydro-3,6-dimethyl-4-oxo-5-pyrimidinyl, 2-oxo-2H-1-benzopyranyl, 3,7-dihydro-1,3-dimethyl-2,6-dioxo-1H-purin-7-yl, 2,3-dihydro-2-oxo-1-benzimidazolyl, or $R^3$ represents a radical of the formula:

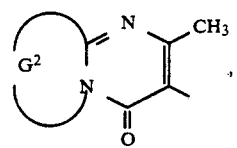
(c-4-a)

wherein $G^2$ represents —CH=CH—CH=CH—, —(CH$_2$)$_4$—, —S—(CH$_2$)$_2$, —S—(CH$_2$)$_3$—, —S—CH=CH—, —N(CH$_2$)$_3$, —N=C(CH$_3$)—CH$_2$—, —N(CH$_3$)—N=C(CH$_3$)—; —N(CH$_3$)—CH=CH— or CH=C(CH$_3$)—O—;

Y represents NH, O or S;

$R^4$ represents hydrogen, $C_{1-4}$alkyl, halophenyl, pyridinyl, halopyridinyl, pyrimidinyl, 1,4-dihydro-2,4-dioxo-3(2H)-pyrimidinyl, 1,4-dihydro-4-oxopyrimidinyl, pyridazinyl, halo-pyridazinyl, 1-methylimidazolyl, thiazolyl, 2-amino-1,3,4-thiadiazolyl, 6-purinyl or imidazo[4,5-c]-pyridinyl;

$Z^1$ and $Z^2$ each independently represent O, NH or a direct bond;

X represents O or S;

$R^5$ represents hydrogen, $C_{1-4}$alkyl, aminophenyl, $C_{1-4}$alkyl-phenyl, pyridinyl, aminopyridinyl, aminopyrazinyl, 1-methylpyrrolyl, furanyl or 1-methylindolyl; and $R^6$ represents phenyl.

4. A compound according to claim 3 wherein:
—$A^1$=$A^2$—$A^3$=$A^4$— represents a bivalent radical having the formula —N=CH—CH=CH— (a-2);
R represents hydrogen;
the oxazolyl moiety has the formula:

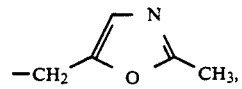

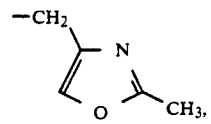

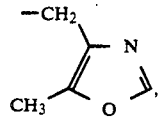

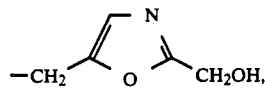

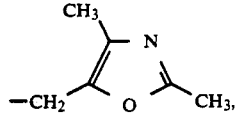

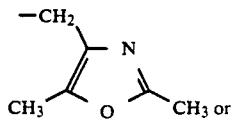

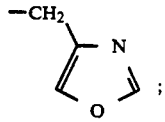

B represents NH, S or CH$_2$;

n is 1; and

L represents hydrogen, C$_{1-4}$alkyl, hydroxyC$_{1-4}$alkyl, propenyl, 3-phenylpropenyl or a radical of the formula:

—Alk—R$^3$ (b-1);

—Alk—Y—R$^4$ (b-2);

—Alk—NH—C(=O)—R$^{5-a}$ (b-3-a);

or

—Alk—C(=O)—Z$^2$—R$^{5-b}$ (b-3-b);

wherein:

each Alk independently represents C$_{1-3}$alkanediyl;

R$^3$ represents phenyl, 4-methoxy-phenyl, 4-hydroxyphenyl, pyridinyl, thienyl, 4,5-dihydro-4-ethyl-5-oxo-1H-tetrazolyl, 2-oxo-2H-1-benzopyranyl, 2-(amino- or methylamino)-3,4-dihydro-3,6-dimethyl-4-oxo-5-pyrimidinyl, 6-purinyl, or R$^3$ represents a radical of the formula:

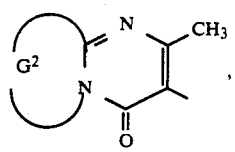

(c-4-a)

wherein G$^2$ represents —CH=CH—CH=CH—, —(CH$_2$)$_4$—, —S—(CH$_2$)$_2$—, —S—(CH$_2$)$_3$—, —S—CH=CH— or —N(CH$_3$)—N=C(CH$_3$)—CH$_2$—;

Y represents NH or O;

R$^4$ represents pyrimidinyl, 5-amino-1,3,4-thiadiazolyl, pyridazinyl, imidazo[4,5-c]pyridinyl or 1,4-dihydro-4-oxo-2-pyrimidinyl;

R$^{5-a}$ represents aminopyrazinyl or furanyl;

Z$^2$ represents O; and

R$^{5-b}$ represents hydrogen.

5. A compound according to claim 4 wherein said compound is a member selected from the group consisting of:

3-[(2-methyl-5-oxazolyl)methyl]-N-(4-piperidinyl)-3H-imidazo[4,5-b]pyridin-2-amine hemihydrate;

N-[1-[2-(4-methoxyphenyl)ethyl]-4-piperidinyl]-3-[(2-methyl-5-oxazolyl)methyl]-3H-imidazo[4,5-b]pyridin-2-amine;

3-[(2-methyl-5-oxazolyl)methyl]-N-[1-[2-(2-thienyl)ethyl]-4-piperidinyl]-3H-imidazo[4,5-b]pyridin-2-amine;

2-[[2-[4-[[3-[(2-methyl-5-oxazolyl)methyl]-3H-imidazo[4,5-b]-pyridin-2-yl]amino]-1-piperidinyl]ethyl]amino]-4(1H)-pyrimidinone (E)-2-butenedioate (2:5); and 9-[(2-methyl-5-oxazolyl)methyl9 -N-(1-methyl-4-piperidinyl)-9H-purin-8-amine.

6. An antiallergic composition comprising a pharmaceutically acceptable carrier and as active ingredient an effective anti-allergic amount of a compound as claimed in claim 1.

7. An antiallergic composition comprising a pharmaceutically acceptable carrier and as active ingredient an effective anti-allergic amount of a compound as claimed in claim 2.

8. An antiallergic composition comprising a pharmaceutically acceptable carrier and as active ingredient an effective anti-allergic amount of a compound as claimed in claim 3.

9. An antiallergic composition comprising a pharmaceutically acceptable carrier and as active ingredient an effective anti-allergic amount of a compound as claimed in claim 4.

10. An antiallergic composition comprising a pharmaceutically acceptable carrier and as active ingredient an effective anti-allergic amount of a compound as claimed in claim 5.

11. A method of treating warm-blooded animals suffering from allergic diseases comprising administering to said warm-blooded animals an effective antiallergic amount of a compound as claimed in claim 1.

12. A method of treating warm-blooded animals suffering from allergic diseases comprising administering to said warm-blooded animals an effective antiallergic amount of a compound as claimed in claim 2.

13. A method of treating warm-blooded animals suffering from allergic diseases comprising administering to said warm-blooded animals an effective antiallergic amount of a compound as claimed in claim 3.

14. A method of treating warm-blooded animals suffering from allergic diseases comprising administering to said warm-blooded animals an effective antiallergic amount of a compound as claimed in claim 4.

15. A method of treating warm-blooded animals suffering from allergic diseases comprising administering to said warm-blooded animals an effective antiallergic amount of a compound as claimed in claim 5.

* * * * *